US012753414B2

(12) United States Patent
Durany Turk et al.

(10) Patent No.: US 12,753,414 B2
(45) Date of Patent: Oct. 6, 2026

(54) VECTOR FOR CO-EXPRESSING GENES OF INTEREST

(71) Applicant: GAT BIOSCIENCES, S.L., Barcelona (ES)

(72) Inventors: Olga Durany Turk, Barcelona (ES); Jordi Segura De Yebra, Barcelona (ES); Jaume Mercade Roca, Barcelona (ES); Maria Teresa Lopez Cerro, Barcelona (ES); Cristina Lopez Paz, Barcelona (ES); Lourdes Tatiana Roque Navarro, Barcelona (ES)

(73) Assignee: GAT BIOSCIENCES, S.L., Barcelona (ES)

( * ) Notice: Subject to any disclaimer, the term of this patent is extended or adjusted under 35 U.S.C. 154(b) by 1440 days.

(21) Appl. No.: 17/053,495

(22) PCT Filed: May 9, 2019

(86) PCT No.: PCT/EP2019/061981

§ 371 (c)(1),
(2) Date: Nov. 6, 2020

(87) PCT Pub. No.: WO2019/215303

PCT Pub. Date: Nov. 14, 2019

(65) Prior Publication Data

US 2021/0230624 A1 Jul. 29, 2021

(30) Foreign Application Priority Data

May 9, 2018 (EP) .................................... 18382320

(51) Int. Cl.
*C12N 15/82* (2006.01)
*C07K 16/00* (2006.01)

(52) U.S. Cl.
CPC .......... *C12N 15/8258* (2013.01); *C07K 16/00* (2013.01); *C07K 2317/52* (2013.01); *C07K 2317/54* (2013.01); *C07K 2319/02* (2013.01)

(58) Field of Classification Search
CPC ............ C12N 15/8258; C12N 15/8216; C12N 15/79; C12N 15/8257; C12N 15/86; C12N 2760/16122; C12N 2760/18522; C12N 2770/10043; C12N 2770/10021; C07K 16/00; C07K 2317/52; C07K 2317/54; C07K 2319/02; C07K 14/005; C07K 16/32; C07K 2317/515; C07K 2317/51; C07K 2319/00; C07K 2317/14; C12P 21/005; C12P 21/00; A61P 31/00; A61P 37/04; A61P 3/00; A61P 35/00; A61K 48/005
See application file for complete search history.

(56) References Cited

FOREIGN PATENT DOCUMENTS

| | | | | |
|---|---|---|---|---|
| CN | 104630255 A | | 5/2015 | |
| CN | 105316356 A | | 2/2016 | |
| WO | 2017129723 A1 | | 8/2017 | |
| WO | WO-2019215303 A1 | * | 11/2019 | ............ C07K 16/00 |

OTHER PUBLICATIONS

Masayuki Onishi, John R Pringle, Robust Transgene Expression from Bicistronic mRNA in the Green Alga *Chlamydomonas reinhardtii,* G3 Genes|Genomes|Genetics, vol. 6, Issue 12, Dec. 1, 2016, pp. 4115-4125 (Year: 2016).*

López-Paz, C., Liu, D., Geng, S. and Umen, J.G. (2017), Identification of Chlamydomonas reinhardtii endogenous genic flanking sequences for improved transgene expression. Plant J, 92: 1232-1244 (Year: 2017).*

Rasala BA, Chao SS, Pier M, Barrera DJ, Mayfield SP. Enhanced genetic tools for engineering multigene traits into green algae. PLoS One. Apr. 7, 2014;9(4):e94028. doi: 10.1371/journal.pone.0094028. PMID: 24710110; PMCID: PMC3978050. (Year: 2014).*

Stevens DR, Rochaix JD, Purton S. The bacterial phleomycin resistance gene ble as a dominant selectable marker in Chlamydomonas. Mol Gen Genet. Apr. 24, 1996;251(1):23-30. doi: 10.1007/BF02174340. PMID: 8628243. (Year: 1996).*

Barahimipour R, Neupert J, Bock R. Efficient expression of nuclear transgenes in the green alga *Chlamydomonas:* synthesis of an HIV antigen and development of a new selectable marker. Plant Mol Biol. Mar. 2016;90(4-5):403-18. (Year: 2016).*

Yubing LiDianyi LiuCristina López-PazBradley JSC OlsonJames G Umen (2016) A new class of cyclin dependent kinase in Chlamydomonas is required for coupling cell size to cell division eLife 5:e10767. (Year: 2016).*

Du S, Li C, Wang Y, Liu C, Ren D, Li Y, Qin Y, Wang M, Sun D, Zhu N, Jin N. Construction and evaluation of a new triple-gene expression cassette vaccinia virus shuttle vector. J Virol Methods. Nov. 2012;185(2):175-83. doi: 10.1016/j.jviromet.2012.06.022. Epub Jul. 2, 2012. PMID: 22766182. (Year: 2012).*

Larrea-Alvarez M, Purton S. Multigenic engineering of the chloroplast genome in the green alga *Chlamydomonas reinhardtii.* Microbiology (Reading). Jun. 2020;166(6):510-515 (Year: 2020).*

Jia et al., A vector for multiple gene co-expression in Chlamydomonas reinhardtii. Algal Research (2016), 20: 53-56 (Year: 2016).*

Kumar et al., Evaluating nuclear transgene expression systems in Chlamydomonas reinhardtii. Algal Research (2013), 2: 321-332 (Year: 2013).*

Tran et al., Synthesis and assembly of a full-length human monoclonal antibody in algal chloroplasts. Biotechnology and Bioengineering (2009), 104: 663-673 (Year: 2009).*

Hempel et al., Algae as Protein Factories: Expression of a Human Antibody and the Respective Antigen in the Diatom Phaeodactylum tricornutum. PloS One (2011), 6(12): e28424 (Year: 2011).*

(Continued)

*Primary Examiner* — Catherine Konopka
(74) *Attorney, Agent, or Firm* — LUCAS & MERCANTI, LLP

(57) ABSTRACT

An expression vector for the co-expression of different polynucleotides in microalgal cells and to the expression cassettes having both polynucleotides is provided. Also provided are a host cell, a method for expressing the proteins of interest and a method for selecting a cell co-expressing two proteins of interest in a stoichiometric manner.

14 Claims, 13 Drawing Sheets

Specification includes a Sequence Listing.

(56) References Cited

OTHER PUBLICATIONS

Lumbreras et al., Efficient foreign gene expression in Chlamydomonas reinhardtii mediated by an endogenous intron. Plant Journal (1998), 14: 441-447 (Year: 1998).*
Arias et al., Production of Recombinant Biopharmaceuticals in Chlamydomonas reinhardtii. International Journal of Plant Biology (2022), 14: 39-42 (Year: 2022).*
Michael Schroda, Good News for Nuclear Transgene Expression in Chlamydomonas. Cells (2019), 8: 1534, pp. 1-19 (Year: 2019).*
Onishi et al., Robust Transgene Expression From Bicistronic mRNA in the Green Alga *Chlamydomonas reinhardtii*, G3 Genes, vol. 6, No. 12, pp. 4115-4125, 2016.
Barahimipour et al., “Efficient Expression of Nuclear Transgenes in Green Alga *Chlamydomonas:* Synthesis of an HIV Antigen and Development of a New Selectable Marker”, Plant Molecular Biology, vol. 90, No. 4, pp. 403-418, 2016.
Lopez-Paz et al., “Identification of Chlamydomonas Reinhardtii Endogenous Genic Flanking Sequences for Improved Transgene Expression”, The Plant Journal 2017, vol. 92, No. 6, pp. 1232-1244, 2017.
Li et al., “A New Class of Cyclin Dependent Kinase in Chlamydomonas is Required for Coupling Cell Size to Cell Division”, eLIFE, vol. 25, No. 5, pp. 1-28, 2016.
Heitzer et al., “Construction of Modular Tandem Expression Vectors for the Green Alga *Chlamydomonas reinhardtii* Using the CRE/LOX-System”, BioTechniques, vol. 43, No. 3, pp. 324-332, 2007.
Dong et al., “A Novel Bicistronic Expression System Composed of the Intraflagellar Transport Protein Gene ift25 and FMDV 2A Sequence Directs Robust Nuclear Gene Expression in Chlamydomonas Reinhardtii”, Applied Microbiology and Biotechnology, vol. 101, No. 10, pp. 4227-4245, 2017.
Jia et al., “A Vector for Multiple Gene Co-Expression in Chlamydomonas Reinhardtii”, Algal Research, vol. 20, pp. 53-56, 2016.
Romero-Campero et al., “Chlamynet: A Chlamydomonas Gene Co-Expression Network Reveals Global Properties of the Transcriptome and the Early Setup of Key Co-Expression Patterns in the Green Lineage”, BMC Genomics, vol. 17, No. 1, pp. 1-28, 2016.
Aoki et al., “ALCOdb: Gene Coexpression Database for Microlgae”, Plant Cell Physiology, vol. 57, No. 1, pp. e3 1-9, 2015.
Mayfield et al., “Expression and Assembly of a Fully Active Antibody in Algae”, PNAS, vol. 100, No. 2, pp. 438-442, 2003.
Rasala et al., Robust Expression and Secretion of Xylanase 1 In Chlamydomonas Reinhardtii by Fusion to a Selection Gene and Processing With the FMDV 2A Peptide, PLoS One, vol. 7, No. 8, pp. 1-11, 2012.
Fischer et al., “The Flanking Regions of PsaD Drive Effcient Gene Expression in the Nucleus of the Green Alga *Chlamydomonas reinhardtii*”, Mol Genet Genomics, vol. 265, No. 5, pp. 888-894, 2001.
International Search Report and Written Opinion for Corresponding International Application No. PCT/EP2019/061981 (15 Pages) (Jun. 3, 2019).
International Preliminary Report on Patentability for Corresponding International Application No. PCT/EP2019/061981 (9 Pages) (Nov. 10, 2020).

* cited by examiner

A.

B.

| transformant | Media (µg/L) | Intracellular (ng/L) |
|---|---|---|
| **19A3** | 0,07 | 0,82 |
| **19A3-1** | 0,26 | 4,66 |
| **19A3-6** | 0,32 | 3,17 |

SEQUENCE LISTING

```
<160> NUMBER OF SEQ ID NOS: 34

<210> SEQ ID NO 1
<211> LENGTH: 1380
<212> TYPE: DNA
<213> ORGANISM: Artificial sequence
<220> FEATURE:
<223> OTHER INFORMATION: Heavy chain of the antibody m5c3

<400> SEQUENCE: 1

accatgaagt gctcctgggt catcttcttt ctgatggccg tcgtcacggg ggtgaactcc     60

gaggcgcagc tgcagcagtc gggggccgag ctggtcaagc ctggcgcctc ggtgaagctg    120

tcgtgcacgg cttcgggctt caacattcag gagacgtaca tgcattgggt caagcagcgc    180

cccgagcagg ggctggagtg gatcggtcgc attgatcccg ctaacggtaa caccaaggac    240

gatccgaagt tccagggtaa ggctagcatt accgtcgata cgagctcgaa cacggcgtac    300

ctgcagctct ccagcctcac gtcggaggac accgctgtct actactgcgc ttcgtcctac    360

gccatggact actggggcca gggtacgtcc gtgaccgtgt cgtcggccaa gacgaccccg    420

ccgagcgtct accccctggc gccgggttcc gccgcgcaga cgaactccat ggtcacgctc    480

ggttgcctgg tgaagggtta cttccccgag ccggtgacgg tcacctggaa ctcggggtcc    540

ctctccagcg gcgtgcatac gtttccggcg gtgctgcaga gcgacctgta cacgctgtcg    600

agctccgtga ccgtcccctc gtccacgtgg ccttcggaga ccgtgacgtg caacgtcgcc    660

catcctgctt cgagcaccaa ggtggataag aagatcgtcc ctcgcgactg cgggtgcaag    720

ccttgcattt gcacggtgcc cgaggtgagc tccgtcttta tcttcccgcc gaagcccaag    780
```

gatgtgctca ccatcacgct gaccccctaag gtcacctgcg tcgtggtcga tattagcaag 840
gacgaccccg aggtgcagtt ctcctggttt gtcgacgatg tcgaggtgca cacggctcag 900
acgcagcccc gcgaggagca gttcaactcc acgtttcgca gcgtgtcgga gctgcctatt 960
atgcatcagg attggctcaa cggtaaggag ttcaagtgcc gcgtgaacag cgccgccttc 1020
cccgccccga tcgagaagac cattagcaag accaagggcc gccccaaggc tccccaggtc 1080
tacacgattc ctcccccctaa ggagcagatg gctaaggata aggtgtcgct gacgtgcatg 1140
attacggatt tttttcctga ggatattacc gtggagtggc agtggaacgg tcagcccgcg 1200
gagaactaca agaacaccca gcctattatg gataccgatg ggtcctactt cgtctactcc 1260
aagctgaacg tgcagaagag caactgggag gccgggaaca ccttcacctg ctcggtgctc 1320
catgagggcc tccataacca ccatacggag aagtccctct cccactcgcc cggtaagtaa 1380

<210> SEQ ID NO 2
<211> LENGTH: 720
<212> TYPE: DNA
<213> ORGANISM: Artificial sequence
<220> FEATURE:
<223> OTHER INFORMATION: light chain of the antibody m5c3

<400> SEQUENCE: 2
accatgaagc tgccggtgcg gctgctggtc ctcgtctttt ggattcctgc ctcgagctcg 60
gacgtcctga tgacccagac gcccctctcc ctccccgtgt cgctgggcga tcaggcgagc 120
atctcctgcc ggagctcgca gagcattgtc cactcgaacg gtaacacgta cctcgagtgg 180
tacctgcaga agaccggtca gtcgccggag ctgctgattt acaaggtgag caaccggctc 240
tcgggtgtgc ccgaccggtt ctcggggtcc gggagcggga ccgatttcac gctcaagatt 300
agccgggtcg aggccgagga cctgggcgtc tactactgct tccagggtag ccacgtgccc 360
ttcaccttcg ggtcgggtac caagctggag atcaagcggg ctgacgcggc gcctacggtg 420
tcgatttttc ctccctcgag cgagcagctg acgtccggtg gtgccagcgt cgtgtgcttt 480
ctcaacaact tttaccccaa ggacatcaac gtcaagtgga agattgatgg tagcgagcgc 540
cagaacgggg tcctcaactc gtggacggac caggactcca aggactcgac ctactcgatg 600
tccagcaccc tgaccctcac gaaggatgag tacgagcgcc acaacagcta cacctgcgag 660
gcgacgcaca agacctccac gtcgcctatt gtgaagagct ttaaccgcaa cgagtgttaa 720

<210> SEQ ID NO 3
<211> LENGTH: 392
<212> TYPE: DNA
<213> ORGANISM: Artificial sequence
<220> FEATURE:
<223> OTHER INFORMATION: sh-Ble gene

<400> SEQUENCE: 3
atggccatgc acatggccaa gctgaccagc gccgttccgg tgctcaccgc gcgcgacgtc 60
gccggagcgg tcgagttctg gaccgaccgg ctcgggttct cccgggactt cgtggaggac 120
gacttcgccg gtgtggtccg ggacgacgtg accctgttca tcagcgcggt ccaggaccag 180
accaggtggt gccggacaac accctggcct gggtgtgggt gcgcggcctg gacgagctgt 240
acgccgagtg gtcggaggtc gtgtccacga acttccggga cgcctccggg ccggccatga 300
ccgagatcgg cgagcagccg tgggggcggg agttcgccct gcgcgacccg gccggcaact 360
gcgtgcactt cgtggccgag gagcaggact ga 392

<210> SEQ ID NO 4
<211> LENGTH: 909
<212> TYPE: DNA
<213> ORGANISM: Artificial sequence
<220> FEATURE:
<223> OTHER INFORMATION: RPL23 promoter, or PL promoter

<400> SEQUENCE: 4
ctctagagca cgtccataat gaaaggtccg tgactcatga agccagcaca cacgtgatga 60
tatcgttccg ctgtggctgg ggtggagcct tcgtcaatac ggtaacaacg ctagctatga 120
tgccggagcc cggaggaatg acgggatgta caaggttgaa ccgctggtga ggtagcagcc 180
ttcaggccta gctgcatgca cccagacgtt gttgtgtgta agcctctgtt cgtgctttac 240
tgcttccaag actctctcgc tacagctgcg tgaaacgaaa gatagtcgat gcgcagcttg 300
gggaagtcct cgtgctgctt gcgcaagctc caattccgcc tccctcctcc caccctcaca 360
ctactcccgc acaccccatc cccacacacc ctgctcccct taacaccgac tgcacctccc 420
ctccggcccc ctccgccccc ctccggcccc ctgcaacact atccctccgc ctcccttcgg 480
cgcagtctcc cgttgtggcc aaccgcgggc gcaaagctga acctcacctt aatcctggtg 540
ctccacacct gtgccaccta cgccctgtca cagggtgaag ataaagccat ggcatctccc 600
gtcgattatt tggctgccgt ttcttggctg ccgcttctcc gaccgctaca cagggtgccc 660
gccaggcgtg gttcaagtgc cagcggggct gccagcgctc tcgccgggtt cgtgccgagt 720
tgaagcaacc tccctgagcc tcctcgcggc ctgcaaatca gtattgataa taccaataca 780
gtaggcatat tcttcaagcc tgctagcgga actagtaagg ccctctgcgc agaagttcgg 840
caaaggctcc agggcccatt ccgtctctct cccgagcgag ctttgacgcg cggcccgcga 900
ctgtttctt 909

<210> SEQ ID NO 5
<211> LENGTH: 687
<212> TYPE: DNA
<213> ORGANISM: Artificial sequence
<220> FEATURE:
<223> OTHER INFORMATION: ferredoxin 1 FDX promoter

<400> SEQUENCE: 5
ggtacctgga ggggtaatcc gtgggggtaa tcgcagggac ccgcaaaccc cccgtctgcg 60
ccgaacttcc gcggcatatc cctggcgacc ccaatcgcga cccaccaact ggcctgcatg 120
atgatactgt gcatgcatgc tggggctcgc acgccgtccg aacccgcgcg caaagctggc 180
ccgcggccac gaaatcgtgg catttgcact tgccggtccg attctactat gccgcgccac 240
gagcagcgac gcgcgaagcc catttcccct gtcatacaaa ttcaggaagc ccatggtcac 300
acattagagc cgcgcatgta ggtcaagctg tctgcgtagg gtcctgtttg cgtggctttg 360
gcatgtgcac ccggcgccca gcgcccgagc gcaattcaag tggttaagac gcctcagaac 420
gcgtaattga atgcatgtgt cattctggaa gggtgtatag agcggtcgag cggaaggctg 480
tccagctcgc gtgcaagcaa ttgtctcgcg acgcccgctc ccgacgagtg cgaccgcccg 540
cgaccgggtt cgctggtgca agtggccaat gcgagcgctg ggcgcagaga aaaaggcgac 600
gtacggcgat gaaggctcca gggcggatgg gcgaggggca accgggataa atggtcctcc 660
tttccccaag gcccgctaca ctcttga 687

<210> SEQ ID NO 6
<211> LENGTH: 473
<212> TYPE: DNA

```
<213> ORGANISM: Artificial sequence
<220> FEATURE:
<223> OTHER INFORMATION: HSP70-RCBS2 chimeric promoter, or AR

<400> SEQUENCE: 6

tcgctgaggc ttgacatgat tggtgcgtat gtttgtatga agctacagga ctgatttggc     60

gggctatgag ggcgggggaa gctctggaag ggccgcgatg gggcgcgcgg cgtccagaag    120

gcgccatacg gcccgctggc ggcacccatc cggtataaaa gcccgcgacc ccgaacggtg    180

acctccactt tcagcgacaa acgagcactt atacatacgc gactattctg ccgctataca    240

taaccactca gctagcttaa gatcccatca agcttgcatg ccgggcgcgc cagaaggagc    300

gcagccaaac caggatgatg tttgatgggg tatttgagca cttgcaaccc ttatccggaa    360

gccccctggc ccacaaaggc taggcgccaa tgcaagcagt tcgcatgcag cccctggagc    420

ggtgccctcc tgataaaccg gccagggggc ctatgttctt tactttttta caa           473


<210> SEQ ID NO 7
<211> LENGTH: 193
<212> TYPE: DNA
<213> ORGANISM: Artificial sequence
<220> FEATURE:
<223> OTHER INFORMATION: 3'UTR of RPL23

<400> SEQUENCE: 7

catatgtaaa ggtgaggcgg gggttcggag ggactagggg aagagttgga cgccagagtg     60

gggcgggttt tcgggcctct gacatgcgcg cgtgccttcc caagcacaac tcaccatctg    120

actcgcatgc tgacggtcct ctgtgtccct tggcccttgc gcgcagattc tgcacgtgta    180

acggtccgcc tgt                                                       193


<210> SEQ ID NO 8
<211> LENGTH: 179
<212> TYPE: DNA
<213> ORGANISM: Artificial sequence
<220> FEATURE:
<223> OTHER INFORMATION: 3'UTR of the RCBS2 gene

<400> SEQUENCE: 8

atggaggcgc tcgttgatct gagccttgcc ccctgacgaa cggcggtgga tggaagatac     60

tgctctcaag tgctgaagcg gtagcttagc tccccgtttc gtgctgatca gtctttttca    120

acacgtaaaa agcggaggag ttttgcaatt ttgttggttg taacgatcct ccgttgatt     179


<210> SEQ ID NO 9
<211> LENGTH: 202
<212> TYPE: DNA
<213> ORGANISM: Artificial sequence
<220> FEATURE:
<223> OTHER INFORMATION: 3'UTR of the FDX gene promoter

<400> SEQUENCE: 9

ggatccggcc tcgaggcgct ttcgccatct gcgggggtcg taggctagaa ctggggttgg     60

ggatcgggct gcttgcatag ccaagcaatt ttccatctgg ccagcaatgg cctagcacta    120

tgagcggttc aagtgtctct tgtgtgttgt gtcgcattgc atggccgtgg tgacctgcaa    180

ttttctgtaa ccggacatgc ag                                             202


<210> SEQ ID NO 10
<211> LENGTH: 146
<212> TYPE: DNA
<213> ORGANISM: Artificial sequence
```

<220> FEATURE:
<223> OTHER INFORMATION: RBCS2 intron sequence

<400> SEQUENCE: 10
gtgagtcgac gagcaagccc ggcggatcag gcagcgtgct tgcagatttg acttgcaacg 60
cccgcattgt gtcgacgaag gcttttggct cctctgtcgc tgtctcaagc agcatctaac 120
cctgcgtcgc cgtttccatt tgcagg 146

<210> SEQ ID NO 11
<211> LENGTH: 60
<212> TYPE: DNA
<213> ORGANISM: Chlamydomonas reinhardtii

<400> SEQUENCE: 11
atggcgcgta ctggcgctct actcctggtc gcgctggcgc ttgcgggctg cgcgcaggct 60

<210> SEQ ID NO 12
<211> LENGTH: 20
<212> TYPE: PRT
<213> ORGANISM: Chlamydomonas reinhardtii

<400> SEQUENCE: 12

Met Ala Arg Thr Gly Ala Leu Leu Leu Val Ala Leu Ala Leu Ala Gly
1 5 10 15

Cys Ala Gln Ala
20

<210> SEQ ID NO 13
<211> LENGTH: 90
<212> TYPE: DNA
<213> ORGANISM: Chlamydomonas reinhardtii

<400> SEQUENCE: 13
atgcatgcac gcaagatggg tgccctcgcg gtgctcgccg tcgcttgcct cgcggcagtg 60
gcatcggttg cgcatgcggc cgacaccaaa 90

<210> SEQ ID NO 14
<211> LENGTH: 30
<212> TYPE: PRT
<213> ORGANISM: Chlamydomonas reinhardtii

<400> SEQUENCE: 14

Met His Ala Arg Lys Met Gly Ala Leu Ala Val Leu Ala Val Ala Cys
1 5 10 15

Leu Ala Ala Val Ala Ser Val Ala His Ala Ala Asp Thr Lys
20 25 30

<210> SEQ ID NO 15
<211> LENGTH: 84
<212> TYPE: DNA
<213> ORGANISM: Chlamydomonas reinhardtii

<400> SEQUENCE: 15
atgtcgctgg cgacgcggcg cttcggcgcc gcagcggcgc ttctagtcgc cgcatgcgtg 60
ctgtgcacag ctcctgcgtg ggcc 84

<210> SEQ ID NO 16
<211> LENGTH: 28
<212> TYPE: PRT
<213> ORGANISM: Chlamydomonas reinhardtii

<400> SEQUENCE: 16

```
Met Ser Leu Ala Thr Arg Arg Phe Gly Ala Ala Ala Ala Leu Leu Val
1               5                   10                  15

Ala Ala Cys Val Leu Cys Thr Ala Pro Ala Trp Ala
            20                  25
```

<210> SEQ ID NO 17
<211> LENGTH: 57
<212> TYPE: DNA
<213> ORGANISM: Artificial sequence
<220> FEATURE:
<223> OTHER INFORMATION: murine signal peptide 1

<400> SEQUENCE: 17

```
atgaagctgc cggtgcggct gctggtcctc gtcttttgga ttcctgcctc gagctcg        57
```

<210> SEQ ID NO 18
<211> LENGTH: 57
<212> TYPE: DNA
<213> ORGANISM: Artificial sequence
<220> FEATURE:
<223> OTHER INFORMATION: murine signal peptide 2

<400> SEQUENCE: 18

```
atgaagtgct cctgggtcat cttctttctg atggccgtcg tcacgggggt gaactcc        57
```

<210> SEQ ID NO 19
<211> LENGTH: 815
<212> TYPE: DNA
<213> ORGANISM: Streptomyces rimosus

<400> SEQUENCE: 19

```
atggacgatg cgttgcgtgc actgcggggt cggtatcccg gttgtgagtg ggttgttgtg     60

gaggatgggg cctcgggggc tggtgtttat cggcttcggg gtggtgggcg ggagttgttt    120

gtcaaggtgg cagctctggg ggccggggtg ggcttgttgg gtgaggctga gcggctggtg    180

tggttggcgg aggtggggat tcccgtacct cgtgttgtgg agggtggtgg ggacgagagg    240

gtcgcctggt tggtcaccga agcggttccg gggcgtccgg ccagtgcgcg gtggccgcgg    300

gagcagcggc tggacgtggc ggtggcgctc gcggggctcg ctcgttcgct gcacgcgctg    360

gactgggagc ggtgtccgtt cgatcgcagt ctcgcggtga cggtgccgca ggcggcccgt    420

gctgtcgctg aagggagcgt cgacttggag gatctggacg aggagcggaa ggggtggtcg    480

ggggagcggc ttctcgccga gctggagcgg actcggcctg cggacgagga tctggcggtt    540

tgccacggtc acctgtgccc ggacaacgtg ctgctcgacc ctcgtacctg cgaggtgacc    600

gggctgatcg acgtggggcg ggtcggccgt gcggaccggc actccgatct cgcgctggtg    660

ctgcgcgagc tggcccacga ggaggacccg tggttcgggc cggagtgttc cgcggcgttc    720

ctgcgggagt acgggcgcgg gtgggatggg gcggtatcgg aggaaaagct ggcgttttac    780

cggctgttgg acgagttctt ctgagggacc tgatg                               815
```

<210> SEQ ID NO 20
<211> LENGTH: 19
<212> TYPE: PRT
<213> ORGANISM: Artificial organism
<220> FEATURE:
<223> OTHER INFORMATION: murine signal peptide 1

<400> SEQUENCE: 20

```
Met Lys Leu Pro Val Arg Leu Leu Val Leu Val Phe Trp Ile Pro Ala
```

```
1               5                   10                  15

Ser Ser Ser


<210> SEQ ID NO 21
<211> LENGTH: 19
<212> TYPE: PRT
<213> ORGANISM: Artificial sequence
<220> FEATURE:
<223> OTHER INFORMATION: murine signal peptide 2

<400> SEQUENCE: 21

Met Lys Cys Ser Trp Val Ile Phe Phe Leu Met Ala Val Val Thr Gly
1               5                   10                  15

Val Asn Ser


<210> SEQ ID NO 22
<211> LENGTH: 538
<212> TYPE: DNA
<213> ORGANISM: Artificial sequence
<220> FEATURE:
<223> OTHER INFORMATION: sh-Ble marker with RBCS2 intron

<400> SEQUENCE: 22

atggccatgc acatggccaa gctgaccagc gccgttccgg tgctcaccgc gcgcgacgtc      60

gccggagcgg tcgagttctg gaccgaccgg ctcgggttct cccgggactt cgtggaggac     120

gacttcgccg gtgtggtccg ggacgacgtg accctgttca tcagcgcggt ccaggaccag     180

gtgagtcgac gagcaagccc ggcggatcag gcagcgtgct tgcagatttg acttgcaacg     240

cccgcattgt gtcgacgaag gcttttggct cctctgtcgc tgtctcaagc agcatctaac     300

cctgcgtcgc cgtttccatt tgcaggacca ggtggtgccg gacaacaccc tggcctgggt     360

gtgggtgcgc ggcctggacg agctgtacgc cgagtggtcg gaggtcgtgt ccacgaactt     420

ccgggacgcc tccgggccgg ccatgaccga gatcggcgag cagccgtggg ggcgggagtt     480

cgccctgcgc gacccggccg gcaactgcgt gcacttcgtg gccgaggagc aggactga       538


<210> SEQ ID NO 23
<211> LENGTH: 109
<212> TYPE: DNA
<213> ORGANISM: Artificial sequence
<220> FEATURE:
<223> OTHER INFORMATION: RPL23- 5'UTR

<400> SEQUENCE: 23

tctctcaccg aggtggtcag caggtaggca aattgcattt tcttttattc atttaggtcc      60

ttgagaactc cgctcacagc tttctcttgt ctgcgcgcag agtgaattc                109


<210> SEQ ID NO 24
<211> LENGTH: 69
<212> TYPE: DNA
<213> ORGANISM: Artificial sequence
<220> FEATURE:
<223> OTHER INFORMATION: FDX 5' UTR

<400> SEQUENCE: 24

ccttgctcac gtagtgtcct tcgtcgccac tcacaacctt caaaagaatt cggcagatct      60

ggcggatcc                                                              69


<210> SEQ ID NO 25
<211> LENGTH: 23
<212> TYPE: DNA
```

<213> ORGANISM: Artificial sequence
<220> FEATURE:
<223> OTHER INFORMATION: 5'UTR RBCS2

<400> SEQUENCE: 25
gagaagtcac tcaacatctt aaa 23

<210> SEQ ID NO 26
<211> LENGTH: 545
<212> TYPE: DNA
<213> ORGANISM: Artificial sequence
<220> FEATURE:
<223> OTHER INFORMATION: 3'cis RPL23 (terminator +flanking regions)

<400> SEQUENCE: 26
gagctttccg gtcccgaccc tcgctcccgt tcatcgcgct cggcgcggca gcagttgtag 60
cggacagcag cagcggcagc aggggccctg ccagcacgaa aggagtagca gcctggggcg 120
gacactgtca gcagagccgg cagccggact gtttgaggtt actcagtgcc aattgcagca 180
tttgagctgc ctccaggcag cggcggcagc agctggaaag tgtggccagt ggcggtttgg 240
atcagcatga ctgtgacgtg ctagataaca gcagcggcag gcaatgagca tgcagaatag 300
cgaggaaccg ggagggttgt gaggagtgga cgaaggggca agcggctctg cccatcgcga 360
gcgaacccgc aacagcgagg gcactcagcc cgtaacgcgc aagtgccctc caccaaacag 420
cagcagcagc aagaaacgca aacagctggg agcatgtcta tttctgcgct gtggcattgc 480
aggtgcttgc cttggacccg tgcggaggga gcatacgtct gcggcgaagc tgcgcctggg 540
gtacc 545

<210> SEQ ID NO 27
<211> LENGTH: 541
<212> TYPE: DNA
<213> ORGANISM: Artificial sequence
<220> FEATURE:
<223> OTHER INFORMATION: 3'cis FDX  terminator +flanking regions

<400> SEQUENCE: 27
aagcttcggt tcgcgtcctt tcctcgcttg ctacgggatc gggagtcggc agggctagaa 60
gacttgggta acacgcgcaa ttcagcaata caggccagcc agggcagcga agggggactt 120
cagcaaggac ctctcgggaa tagtggaaga gctaggaggg gtacagcagt agagatcgag 180
gggtccagct cacagttcta ttacgtcgtt cgtggggacg aactgggtcg aggcgctacg 240
gactcgaaat gacggcagag ggtggcaagg aaggggagca ccactgtgag cagttgcagc 300
ggcacataca ctacgtctct tggccttaag cacagccagc acacttgtac ggggcaacag 360
tagccccgaa gcagcctgat gcagtcacac cgtgccgggc cagtgttaac aaggaagggc 420
aggcaccagg gcgagggcag gcgcggcaaa actcgccggt tcctgacacg gtgacacgca 480
ggtatacggt gacagctcag ctagtgatac cagctgctcc gcgttctgag gagaggagct 540
c 541

<210> SEQ ID NO 28
<211> LENGTH: 42
<212> TYPE: DNA
<213> ORGANISM: Artificial sequence
<220> FEATURE:
<223> OTHER INFORMATION: 3' cis RBCS2 flanking region

<400> SEQUENCE: 28
ttggcctctt tctccatggg cgggctgggc gtatttgaag cg 42

<210> SEQ ID NO 29
<211> LENGTH: 1018
<212> TYPE: DNA
<213> ORGANISM: Artificial sequence
<220> FEATURE:
<223> OTHER INFORMATION: RPL23 promoter + 5'UTR

<400> SEQUENCE: 29
ctctagagca cgtccataat gaaaggtccg tgactcatga agccagcaca cacgtgatga 60
tatcgttccg ctgtggctgg ggtggagcct tcgtcaatac ggtaacaacg ctagctatga 120
tgccggagcc cggaggaatg acgggatgta caaggttgaa ccgctggtga ggtagcagcc 180
ttcaggccta gctgcatgca cccagacgtt gttgtgtgta agcctctgtt cgtgctttac 240
tgcttccaag actctctcgc tacagctgcg tgaaacgaaa gatagtcgat gcgcagcttg 300
gggaagtcct cgtgctgctt gcgcaagctc caattccgcc tccctcctcc caccctcaca 360
ctactcccgc acaccccatc cccacacacc ctgctcccct taacaccgac tgcacctccc 420
ctccggcccc ctccgccccc ctccggcccc ctgcaacact atccctccgc ctcccttcgg 480
cgcagtctcc cgttgtggcc aaccgcgggc gcaaagctga acctcacctt aatcctggtg 540
ctccacacct gtgccaccta cgccctgtca cagggtgaag ataaagccat ggcatctccc 600
gtcgattatt tggctgccgt ttcttggctg ccgcttctcc gaccgctaca cagggtgccc 660
gccaggcgtg gttcaagtgc cagcggggct gccagcgctc tcgccgggtt cgtgccgagt 720
tgaagcaacc tccctgagcc tcctcgcggc ctgcaaatca gtattgataa taccaataca 780
gtaggcatat tcttcaagcc tgctagcgga actagtaagg ccctctgcgc agaagttcgg 840
caaaggctcc agggcccatt ccgtctctct cccgagcgag ctttgacgcg cggcccgcga 900
ctgtttcttt ctctcaccga ggtggtcagc aggtaggcaa attgcatttt cttttattca 960
tttaggtcct tgagaactcc gctcacagct ttctcttgtc tgcgcgcaga gtgaattc 1018

<210> SEQ ID NO 30
<211> LENGTH: 738
<212> TYPE: DNA
<213> ORGANISM: Artificial sequence
<220> FEATURE:
<223> OTHER INFORMATION: 3'UTR RPL23 containing
3'UTR/terminator+flanking region

<400> SEQUENCE: 30
catatgtaaa ggtgaggcgg gggttcggag ggactagggg aagagttgga cgccagagtg 60
gggcgggttt tcgggcctct gacatgcgcg cgtgccttcc caagcacaac tcaccatctg 120
actcgcatgc tgacggtcct ctgtgtccct tggcccttgc gcgcagattc tgcacgtgta 180
acggtccgcc tgtgagcttt ccggtcccga ccctcgctcc cgttcatcgc gctcggcgcg 240
gcagcagttg tagcggacag cagcagcggc agcaggggcc ctgccagcac gaaaggagta 300
gcagcctggg gcggacactg tcagcagagc cggcagccgg actgtttgag gttactcagt 360
gccaattgca gcatttgagc tgcctccagg cagcggcggc agcagctgga aagtgtggcc 420
agtggcggtt tggatcagca tgactgtgac gtgctagata acagcagcgg caggcaatga 480
gcatgcagaa tagcgaggaa ccgggagggt tgtgaggagt ggacgaaggg gcaagcggct 540
ctgcccatcg cgagcgaacc cgcaacagcg agggcactca gcccgtaacg cgcaagtgcc 600
ctccaccaaa cagcagcagc agcaagaaac gcaaacagct gggagcatgt ctatttctgc 660
gctgtggcat tgcaggtgct tgccttggac ccgtgcggag ggagcatacg tctgcggcga 720
agctgcgcct ggggtacc 738

<210> SEQ ID NO 31
<211> LENGTH: 756
<212> TYPE: DNA
<213> ORGANISM: Artificial sequence
<220> FEATURE:
<223> OTHER INFORMATION: FDX promoter + 5'UTR

<400> SEQUENCE: 31
ggtacctgga ggggtaatcc gtgggggtaa tcgcagggac ccgcaaaccc cccgtctgcg 60
ccgaacttcc gcggcatatc cctggcgacc ccaatcgcga cccaccaact ggcctgcatg 120
atgatactgt gcatgcatgc tggggctcgc acgccgtccg aacccgcgcg caaagctggc 180
ccgcggccac gaaatcgtgg catttgcact tgccggtccg attctactat gccgcgccac 240
gagcagcgac gcgcgaagcc catttcccct gtcatacaaa ttcaggaagc ccatggtcac 300
acattagagc cgcgcatgta ggtcaagctg tctgcgtagg gtcctgtttg cgtggctttg 360
gcatgtgcac ccggcgccca gcgcccgagc gcaattcaag tggttaagac gcctcagaac 420
gcgtaattga atgcatgtgt cattctggaa gggtgtatag agcggtcgag cggaaggctg 480
tccagctcgc gtgcaagcaa ttgtctcgcg acgcccgctc ccgacgagtg cgaccgcccg 540
cgaccgggtt cgctggtgca agtggccaat gcgagcgctg ggcgcagaga aaaaggcgac 600
gtacggcgat gaaggctcca gggcggatgg gcgaggggca accgggataa atggtcctcc 660
tttccccaag gcccgctaca ctcttgacct tgctcacgta gtgtccttcg tcgccactca 720
caaccttcaa aagaattcgg cagatctggc ggatcc 756

<210> SEQ ID NO 32
<211> LENGTH: 743
<212> TYPE: DNA
<213> ORGANISM: Artificial sequence
<220> FEATURE:
<223> OTHER INFORMATION: 3'UTR FDX containing 3'UTR/terminator+flanking region

<400> SEQUENCE: 32
ggatccggcc tcgaggcgct ttcgccatct gcgggggtcg taggctagaa ctggggttgg 60
ggatcgggct gcttgcatag ccaagcaatt ttccatctgg ccagcaatgg cctagcacta 120
tgagcggttc aagtgtctct tgtgtgttgt gtcgcattgc atggccgtgg tgacctgcaa 180
ttttctgtaa ccggacatgc agaagcttcg gttcgcgtcc tttcctcgct tgctacggga 240
tcgggagtcg gcagggctag aagacttggg taacacgcgc aattcagcaa tacaggccag 300
ccagggcagc gaagggggac ttcagcaagg acctctcggg aatagtggaa gagctaggag 360
gggtacagca gtagagatcg aggggtccag ctcacagttc tattacgtcg ttcgtgggga 420
cgaactgggt cgaggcgcta cggactcgaa atgacggcag agggtggcaa ggaaggggag 480
caccactgtg agcagttgca gcggcacata cactacgtct cttggcctta agcacagcca 540
gcacacttgt acggggcaac agtagccccg aagcagcctg atgcagtcac accgtgccgg 600
gccagtgtta acaaggaagg gcaggcacca gggcgagggc aggcgcggca aaactcgccg 660
gttcctgaca cggtgacacg caggtatacg gtgacagctc agctagtgat accagctgct 720
ccgcgttctg aggagaggag ctc 743

<210> SEQ ID NO 33
<211> LENGTH: 650

```
<212> TYPE: DNA
<213> ORGANISM: Artificial sequence
<220> FEATURE:
<223> OTHER INFORMATION: AR promoter +5'UTR

<400> SEQUENCE: 33

tcgctgaggc ttgacatgat tggtgcgtat gtttgtatga agctacagga ctgatttggc     60

gggctatgag ggcgggggaa gctctggaag ggccgcgatg gggcgcgcgg cgtccagaag    120

gcgccatacg gcccgctggc ggcacccatc cggtataaaa gcccgcgacc ccgaacggtg    180

acctccactt tcagcgacaa acgagcactt atacatacgc gactattctg ccgctataca    240

taaccactca gctagcttaa gatcccatca agcttgcatg ccgggcgcgc cagaaggagc    300

gcagccaaac caggatgatg tttgatgggg tatttgagca cttgcaaccc ttatccggaa    360

gcccccctggc ccacaaaggc taggcgccaa tgcaagcagt tcgcatgcag cccctggagc    420

ggtgccctcc tgataaaccg gccagggggc ctatgttctt tacttttttta caagagaagt    480

cactcaacat cttaaaatgg ccaggtgagt cgacgagcaa gcccggcgga tcaggcagcg    540

tgcttgcaga tttgacttgc aacgcccgca ttgtgtcgac gaaggctttt ggctcctctg    600

tcgctgtctc aagcagcatc taaccctgcg tcgccgtttc catttgcagg                650


<210> SEQ ID NO 34
<211> LENGTH: 221
<212> TYPE: DNA
<213> ORGANISM: Artificial sequence
<220> FEATURE:
<223> OTHER INFORMATION: 3'UTR RBC2 containing 3'UTR/terminator+flanking
      region

<400> SEQUENCE: 34

atggaggcgc tcgttgatct gagccttgcc ccctgacgaa cggcggtgga tggaagatac     60

tgctctcaag tgctgaagcg gtagcttagc tccccgtttc gtgctgatca gtcttttttca    120

acacgtaaaa agcggaggag ttttgcaatt ttgttggttg taacgatcct ccgttgattt    180

tggcctcttt ctccatgggc gggctgggcg tatttgaagc g                        221
```

VECTOR FOR CO-EXPRESSING GENES OF INTEREST

CROSS REFERENCE TO RELATED APPLICATION

This Application is a 371 of PCT/EP2019/061981, filed on May 9, 2019 which, in turn, claimed the priority of European Patent Application No. 18382320.2 filed on May 9, 2018, both applications are incorporated herein by reference.

REFERENCE TO A SEQUENCE LISTING SUBMITTED ELECTRONICALLY VIA EFS-WEB

The content of the electronically submitted sequence listing, file name: 20ABG-1048_SequenceListing.txt; size: 22,266 bytes; and date of creation: Nov. 5, 2020, filed herewith, is incorporated herein by reference in its entirety.

TECHNICAL FIELD OF THE INVENTION

The present invention relates to a method for improving co-expression of more than one polynucleotide or protein in microalgae.

BACKGROUND OF THE INVENTION

Several strategies may be employed in order to achieve multiple recombinant gene expression such as use of multiple vectors with different selection markers, a single vector with a polycistronic mRNA or a single vector producing multiple RNAs. Multiple vectors results in very different expression patterns since random genome insertion results in transformants with different expression levels. Large screenings need to be done since probability of having both genes expressed at the same level is low and this is particularly true for *Chlamydomonas* where high frequency of transgene silencing is observed. The use of a single vector may involve having a duplicate strong promoter/UTR, but this strategy introduces the risk of silencing and recombination. Production of two separate proteins from dicistronic genes has been achieved with viral FMDV2A sequences (Rasala et al. 2012. PLOS One 7), however, the presence in some cases of not processed full-length proteins could become a limitation (López-Paz et al. 2017. Plant J. 92:1232-1244). Bicistronic mRNAs containing a non-structured junction sequence between the two ORFs has also been described, but in this case the expression of downstream gene was lower than upstream gene (Onishi and Pringle 2016. G3 (Bethesda) 6:4115-4125). Therefore, when high levels of expression of a Gene of Interest (GOI) are desired, the use of a single promoter for each gene is probably the preferred option.

Co-expression of subunits is an important requirement in the study and production of protein complexes. When subunits of protein complex are expressed separately they may not be soluble, active or stable, therefore a system to co-express proteins in a stoichiometric manner is a highly desirable tool.

The complex nature of the mechanisms leading to protein co-expression needs designing new strategies that allow for successful expression, assembly and secretion of complex proteins.

SUMMARY OF THE INVENTION

The authors of the present invention have developed a microalgae expression vector containing different promoter and regulatory regions to co-express different polynucleotides and/or proteins simultaneously from the same vector. In the case of the study and production of protein complexes, it is an important requirement that the different subunits of the complex are coexpressed at the same time and with similar efficiency. When subunits of protein complex are expressed separately they may not be soluble, active or stable, therefore the inventor's system to co-express proteins in a stoichiometric manner is a highly desirable tool.

In a first aspect, the invention relates to an expression vector for the co-expression of a first and second polynucleotides of interest in microalgal cells, wherein said first and second polynucleotides of interest are provided respectively in a first and second expression cassettes, each expression cassette comprising a 5' cis regulatory region and a 3' cis regulatory region operatively linked with the first and second polynucleotides and wherein both the 5' and 3' cis regulatory regions of the first expression cassette are different from the 5' and 3' cis regulatory regions of the second expression cassette, wherein the 5' cis regulatory regions comprise a sequence selected from the group consisting of a HSP70A/RBCS2 chimeric promoter, the RPL23 gene promoter and the FDX gene promoter and the 3' cis regulatory regions comprise a sequence selected from the 3'UTR of the RBCS2 gene, the 3'UTR of the RPL23 gene and 3'UTR of the FDX gene.

In a second aspect, the invention relates to a host cell comprising a vector according to the invention.

In a third aspect, the invention relate to the use of a vector according to the invention or a host cell according to the invention for simultaneously co-expressing the first and second polynucleotides of interest.

In a fourth aspect, the invention relates to a method for co-expressing two polynucleotides of interest which comprises growing a cell carrying a vector according to the invention in conditions suitable for allowing the expression of the polynucleotides of interest.

In a fifth aspect, the invention relates to a method for selecting a cell co-expressing in a stoichiometric manner two proteins of interest, comprising a) transforming a cell with a vector according to the invention b) detecting the expression of the two proteins of interest, and c) selecting a cell expressing the two proteins of interest in a stoichiometric manner.

BRIEF DESCRIPTION OF THE FIGURES

FIG. 1A shows FM-zeo$^r$ vector map. FIG. 1B shows Schematics of heavy chain (HC) and FIG. 1C shows light chain (LC). 5'cis regulatory regions (promoter+5'UTR) are represented as rectangles with arrowheads and 3'cis regulatory regions (3'UTR and flanking 3'regions, including terminators) are represented as rectangles. Indicated genic regions are AR: HSP70A-RBCS2 chimeric promoter (includes also 5'UTR and first intron of RBCS2); RPL23: cis regulatory regions of ribosomal protein RPL23; FDX: Ferredoxin1 cis regulatory elements; CDRS: complementarity-determining regions; ss: signal sequence, 3'T: 3'UTR+terminator), ir: intron 1 RBCS2.

FIG. 3A shows 12 μl (1700× concentrated clarified media from 19A3 transformant and different amounts of a mouse monoclonal antibody (C+) were run under reducing conditions to detect heavy and light chains. Two different exposure times are shown. FIG. 3B shows 28 μl of 80× concentrated culture from different UVM4 positive transformants was loaded and ran under reducing conditions and FIG. 3C shows non reducing conditions (Left panel). A more accurate expression of both Light (C, middle panel) and heavy chain (C, right panel) was performed with clone UVM4-2. Purified m5C3 (produced in mammalian cells) was used as a control-(HC+LC) 2: complete mAb. HC: heavy chain. LC: light chain. For detection of light chain a primary antibody anti-mouse IgG, f(ab') 2 fragment specific was used. For detection of heavy chain an anti-mouse IgG, was used.

FIG. 5A shows Confirmation by Sandwich ELISA of mAb increased expression level of the six selected 19A3 transformants. Cells were grown to late log phase and assay was performed only with culture media. Standard deviations of five technical replicates are presented as error bars. FIG. 5B shows Immunoblot of 19A3 clone and selected retransformantS (19A3-1 and 19A3-6) under reducing (left and middle pannel) and non reducing conditions (right pannel). Non transformed wild type control (CC-124) and m5C3 purified antibody are included as a positive and negative controls respectively. * indicates non specific binding.

FIG. 6A shows Cells were grown to late log phase of growth and Sandwich ELISA assay was performed with cell extracts (white) or culture media (black) (A). Results are expressed in RLU. Standard deviations of three technical replicates are presented as error bars. FIG. 6B shows A standard curve with purified m5C3 was included to estimate expression in transformants.

FIG. 7A shows Sandwich ELISA of selected clones (19A3-1, 19A3-6, UVM4-2) was performed to quantify extracellular (top panel) and intracellular concentration (lower panel) of mAb at different stages of cell culture, time shown in hours (h). FIG. 7B shows Inmmnoblot of 19A3-1, 19A-6 and UVM4-2 selected transformants at different culture stages under non-reducing or reducing conditions as shown in FIG. 7C. Primary antibody anti-mouse IgG, F(ab') 2 fragment specific. 12 μl of 80× concentrated culture media were loaded in each lane. A low exposure (top) and high exposure (bottom) is shown for each immunoblot. (HC+LC) 2: complete mAb. HC: heavy chain. LC: light chain. FIG. 7D shows Growth curves obtained by OD750 nm monitoring every 24 h.

DETAILED DESCRIPTION OF THE INVENTION

Figure 1:
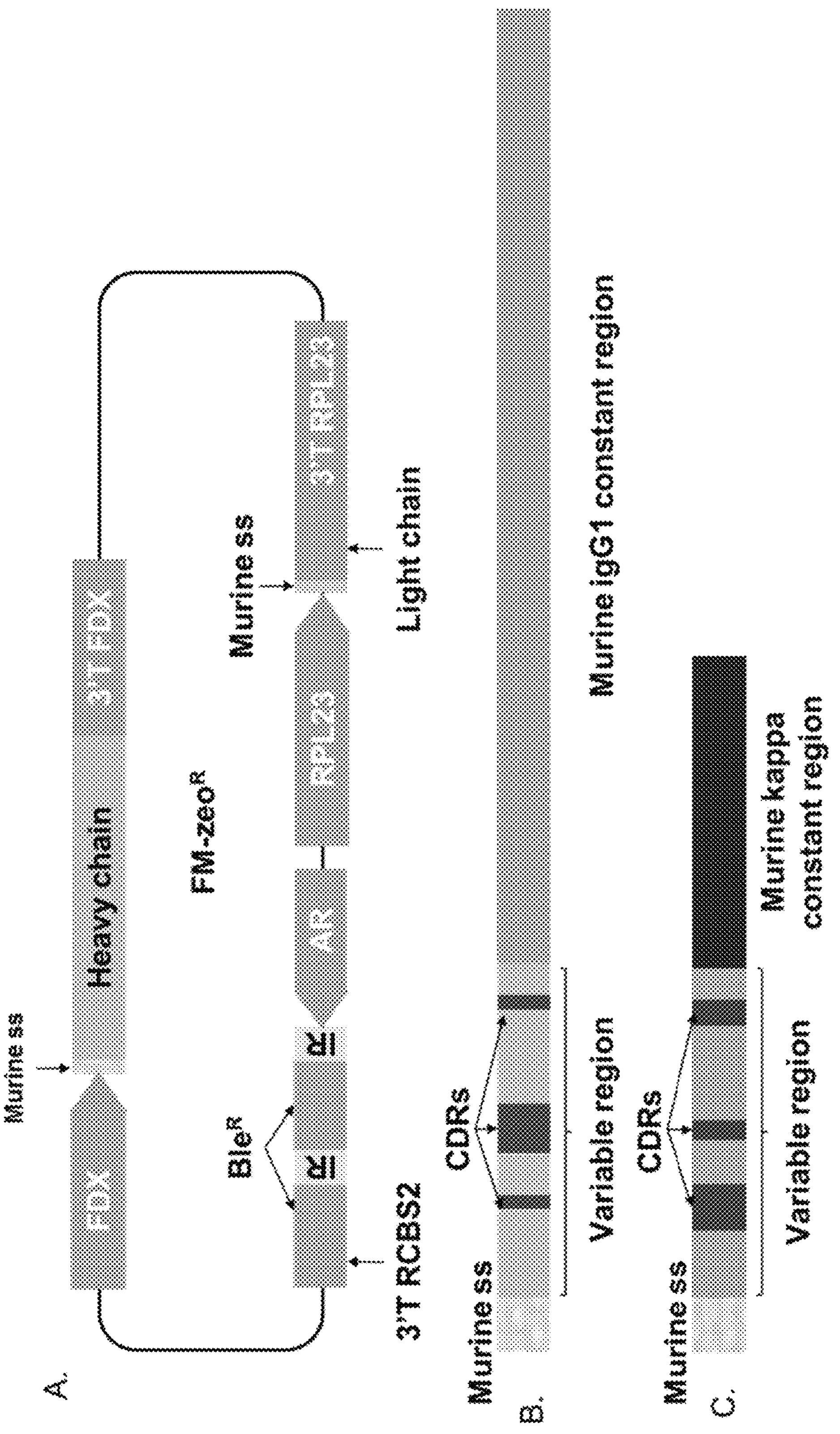
FIGS. 1A-C. Schematic representation of the vector used for the expression in *Chlamydomonas* of murine 5C3 monoclonal antibody (mAB).

The inventors have developed a microalgae expression vector containing different regulatory regions to co-express different proteins simultaneously from the same vector.

Expression Vector

In a first aspect the invention relates to an expression vector for the co-expression of a first and second polynucleotides of interest in microalgal cells, wherein said first and second polynucleotides of interest are provided respectively in a first and second expression cassettes, each expression cassette comprising a 5' cis regulatory region and a 3' cis regulatory region operatively linked with the first and second polynucleotides and wherein both the 5' and 3' cis regulatory regions of the first expression cassette are different from the 5' and 3' cis regulatory regions of the second expression cassette, wherein the 5' cis regulatory regions comprise a sequence selected from the group consisting of a HSP70A/RBCS2 chimeric promoter, the RPL23 gene promoter and the FDX gene promoter and the 3' cis regulatory regions comprise a sequence selected from the 3'UTR of the RBCS2 gene, the 3'UTR of the RPL23 gene and 3'UTR of the FDX gene.

As it is used herein, the term "vector" or "expression vector" refers to a replicative DNA construct used for expressing at least one polynucleotide in a cell, preferably a eukaryotic cell, more preferably a microalga. The choice of expression vector will depend upon the choice of host. A wide variety of expression host/vector combinations can be employed. Useful expression vectors for eukaryotic hosts include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages. In a preferred embodiment, the vector is suitable for expression in microalga. Preferred vectors for this invention are vectors developed for algae such as the vectors commonly known by the skilled person such as aspChlamy_4 vector (Invitrogen), or vectors available through *Chlamydomonas* center. These vectors may contain an additional independent cassette to express a selectable marker that will be used to initially selecting clones that have incorporated the exogenous DNA during the transformation protocol. The expression vector preferably contains an origin of replication in microalga. The expression vector can also contain one or more multiple cloning sites.

The expression vector may also contain an origin of replication in prokaryotes, necessary for vector propagation in bacteria. Additionally, the expression vector can also contain a selection gene for bacteria, for example, a gene encoding a protein conferring resistance to an antibiotic, for example, ampicillin, kanamycin, chloramphenicol, etc. The expression vector can also contain one or more multiple cloning sites. A multiple cloning site is a polynucleotide sequence comprising one or more unique restriction sites. Non-limiting examples of the restriction sites include EcoRI, SacI, KpnI, SmaI, XmaI, BamHI, XbaI, HincII, PstI, SphI, HindIII, AvaI, or any combination thereof.

As it is used herein, the term "polynucleotide" refers to a single-stranded or double-stranded polymer having deoxyribonucleotide or ribonucleotide bases. In a preferred embodiment, the polynucleotide has ribonucleotide bases. In another preferred embodiment, the polynucleotide has deoxyribonucleotide bases.

The polynucleotide or polynucleotides expressed in the vector of the invention as well as the RNA or DNA constructs necessary for preparing the expression vector of the invention can be obtained by means of conventional molecular biology methods included in general laboratory manuals, for example, in "Molecular cloning: a laboratory manual" (Joseph Sambrook, David W. Russel Eds. 2001, 3rd ed. Cold Spring Harbor, New York) or in "Current protocols in molecular biology" (F. M. Ausubel, R. Brent, R. E. Kingston, D. D. Moore, J. A. Smith, J. G. Seidman and K. Struhl Eds, vol. 2. Greene Publishing Associates and Wiley Interscience, New York, N. Y. Updated in September 2006). Useful vectors for microalgal cells are for example RPL23: Luc: RPL23 (López-Paz et al. 2017. Plant J. 92:1232-1244), pGenD-Ble (Fischer N, Rochaix JD 2001 Mol Gen Genet 265:888-894), pChlamy_4vector (invitrogen) pChlamy_4 vector (Invitrogen), or vectors available through *Chlamydomonas* center.

As disclosed herein the term "co-expression" refers to the simultaneous expression of at least two polynucleotides of interest. The term "polynucleotide of interest" refers to any polynucleotides the expression of which in a cell is to be achieved. The expression of the polynucleotides of interest may take place at similar or different levels. In a preferred embodiment the first polynucleotide of interest is expressed at the same level as the second polynucleotide of interest. In another preferred embodiment one of the polynucleotides of interest is expressed at least 1%, at least 2%, at least 3%, at least 4%, at least 5%, at least 6%, at least 7%, at least 8%, at least 9%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or more than the second polynucleotide of interest. In a more preferred embodiment, the two polynucleotides of interest are co-expressed stoichiometrically. In a particular embodiment at least one of the polynucleotides of interest encodes a protein of interest. In another embodiment the two polynucleotides of interest encode a protein of interest. The co-expression of the proteins of interest may take place at similar or different levels. In a preferred embodiment the first protein of interest is expressed at the same level as the second protein of interest. In another preferred embodiment one of the proteins of interest is expressed at least 1%, at least 2%, at least 3%, at least 4%, at least 5%, at least 6%, at least 7%, at least 8%, at least 9%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or more than the second protein of interest. In a preferred embodiment, the two proteins of interest are co-expressed stoichiometrically.

Non-limiting techniques to measure the level of expression of a gene of interest include any known in the art for detecting the expression of a gene and can be based on detecting mRNA or protein. Methods for detecting mRNA are well known in the art and include without limitation, standard assays for determining mRNA expression levels such as qPCR, RT-PCR, RNA protection analysis, Northern blot, RNA dot blot, in situ hybridization, microarray technology, tag based methods such as serial analysis of gene expression (SAGE) including variants such as LongSAGE and SuperSAGE, microarrays, fluorescence in situ hybridization (FISH), including variants such as Flow-FISH, qFISH and double fusion FISH (D-FISH), and the like. Preferably quantitative or semi-quantitative RT-PCR is preferred. Real-time quantitative or semi-quantitative RT-PCR is particularly advantageous.

Virtually any conventional method can be used within the frame of the invention to detect and quantify the levels of proteins. By way of a non-limiting illustration, the expression levels are determined by means of antibodies with the capacity for binding specifically to the protein to be determined (or to fragments thereof containing the antigenic determinants) and subsequent quantification of the resulting antigen-antibody complexes. The antibodies that are going to be used in this type of assay can be, for example, polyclonal sera, hybridoma supernatants or monoclonal antibodies, antibody fragments, Fv, Fab, Fab' and F(ab') 2, scFv, diabodies, triabodies, tetrabodies and humanized antibodies. At the same time, the antibodies may or may not be labeled. Illustrative, but non-exclusive, examples of markers that can be used include radioactive isotopes, enzymes, fluorophores, chemoluminescent reagents, enzyme cofactors or substrates, enzyme inhibitors, particles, dyes, etc. There is a wide variety of well-known assays that can be used in the present invention, using non-labeled antibodies (primary antibody), labeled antibodies (secondary antibodies); these techniques include Western-blot or immunoblot, ELISA (enzyme-linked immunosorbent assay), RIA (radioimmunoassay), competitive EIA (enzyme immunoassay), DAS-ELISA (double antibody sandwich ELISA), immunocytochemical and immunohistochemical techniques, immunofluorescence, techniques based on the use of biochips or protein microarrays including specific antibodies or assays based on the colloidal precipitation in formats such as reagent strips. Other forms of detecting and quantifying the proteins include affinity chromatography techniques, ligand-binding assays, etc.

In a preferred embodiment the polynucleotide of interest encodes a protein of interest. The term "protein of interest" refers to any protein the expression of which in a cell is to be achieved. In another preferred embodiment, the protein of interest is heterologous. Heterologous sequence could be a sequence that is derived from a different gene or from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous." In a preferred embodiment, the protein of interest is in the form of a precursor. The term "precursor" refers to a polypeptide which, once processed, can give rise to a protein of interest. In a particular embodiment, the precursor of the protein of interest is a polypeptide comprising a signal sequence or signal peptide. In a preferred embodiment, the vector co-expresses two different proteins of interest. In another preferred embodiment, the first and second proteins of interest are the two different subunits of a heterodimeric protein.

"Heterodimeric protein", as used herein relates to a macromolecular complex formed by two different protein monomers, or single proteins, which are usually non-covalently bound.

In another preferred embodiment, the first and second proteins of interest are the two subunits of a homodimeric protein, complex formed by two identical proteins.

In a more preferred embodiment the first and second subunits are the heavy chain and the light chain of an antibody. As it is used herein, the term "antibody" refers to a protein including at least one immunoglobulin variable region, for example, an amino acid sequence providing an immunoglobulin variable domain or a sequence of the immunoglobulin variable domain. An antibody can include, for example, a variable heavy chain (H) region (herein abbreviated as VH) and a variable light chain (L) region (herein abbreviated as VL). Typically, an antibody includes two variable heavy chain regions and two variable light chain regions. The term "antibody" encompasses antigen-binding antibody fragments (for example, single-chain antibodies, Fab fragments, F(ab') 2 fragments, Fd fragments, Fv fragments and dAb fragments) as well as whole antibodies, for example, intact and/or full length immunoglobulins of the IgA, IgG types (for example, IgG1, IgG2, IgG3, IgG4), IgE, IgD, IgM (as well as subtypes thereof). The variable heavy and light chain regions can additionally be subdivided into hypervariability regions, referred to as "complementarity determining regions" ("CDR"), mixed together with more conserved regions, referred to as "framework regions" (FR). The extension of FRs and CDRs has been precisely defined (see Kabat, E. A., et al. (1991) Sequences of Proteins of Immunological Interest, Fifth Edition, The United States Department of Health and Human Services, NIH Publication No. 91-3242; and Chothia, C. et al. (1987) *J. Mol. Biol.* 196:901-917). Kabat definitions are used in the present document. Each variable heavy and light chain region is typically made up of three CDRs and four FRs, organized from the amino end to the carboxyl end in the following order: FR1, CDR1, FR2, CDR2, FR3, CDR3, FR4. The antibody VH or VL chain can furthermore include all or part of a heavy chain or light chain constant region to thereby form a heavy chain (HC) or light chain (LC immunoglobulin, respectively. Immunoglobulin light and heavy chains can be bound by disulfide bridges. The heavy chain constant region typically includes three constant domains, CH1, CH2 and CH3. The light chain constant region typically includes a CL domain. The variable heavy and light chain region contains a binding domain interacting with an antigen. The constant regions of the antibodies typically mediate the binding of the antibody to host tissues or factors, including various cells of the immune system (for example, effector cells) and the first component (C1q) of the conventional complement system. The term antibody encompasses both antibodies formed by heavy chains and light chains and single-chain antibodies. Therefore, in a particular embodiment the gene of interest encodes a single-chain antibody or a precursor thereof. In another preferred embodiment, the gene of interest encodes an antibody heavy chain or a precursor thereof. In another preferred embodiment, the gene of interest encodes an antibody light chain or a precursor thereof.

As it is used herein, the term "heavy chain" or "HC" encompasses both a full length heavy chain and fragments thereof. A full length heavy chain includes a variable region domain, $V_H$, and three constant region domains, $C_H1$, $C_H2$ and $C_H3$. The $V_H$ domain is at the amino terminal end of the polypeptide, and the $C_H3$ domain is at the carboxyl terminal end.

As it is used herein, the term "light chain" encompasses a full length light chain and fragments thereof. A full length light chain includes a variable region domain, $V_L$, and a constant region domain, $C_L$. Like the heavy chain, the variable light chain region domain is at the amino terminal end of the polypeptide.

As it is used herein, the term "single-chain antibody" refers to a molecule modified by means of genetic engineering containing the variable light chain region and the variable heavy chain region bound by means of a suitable peptide linker, formed as a genetically fused single-chain molecule.

In a still more preferred embodiment the antibody is m5c3 which specifically binds to S1004.

In a preferred embodiment the first and second subunits are codon optimized for expression in microalgal cells.

The term "codon optimised" as referred to herein relates to the alteration of codons in nucleic acid molecules to reflect the typical codon usage of the host organism, in the present case humans, without altering the polypeptide encoded by the DNA, to improve expression.

A plethora of methods and software tools for codon optimisation are known to the skilled person. Codon-optimised nucleic acids for use according to the present invention can be prepared by replacing the codons of the nucleic acid encoding the immunogen by "microalgae" codons, i.e., the codons are those that appear frequently in highly expressed microalgae genes.

In a preferred embodiment of the protein of interest, the heavy chain of the antibody has the sequence shown in SEQ ID NO: 1 and the light chain of the antibody has the sequence shown in SEQ ID NO: 2. As disclosed herein, SEQ ID NO 1 or 2 may contain a sequence for a restriction site at their 5' or 3'end.

The expression vector of the invention is suitable for the co-expression of a first and second protein of interest in microalgae cells. The term "microalgae cell" or "microalga" is used such that it refers not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein. Microalga as used herein relates to large and diverse group of simple, typically autotrophic organisms, ranging from unicellular to multicellular forms, microscopic algae, typically found in freshwater and marine systems. Examples of suitable microalgae for expressing the vector of the invention, include microalgae from the phylums *Cyanophyta, Chlorophyta, Rhodophyta, Heterokontophyta*, and *Haptophyta*. The algae from the phylum *Cyanophyta* can be *Spirulina* (*Arthrospira*), *Aphanizomenon* flos-aquae, *Anabaena cylindrica* or *Lyngbya majuscule*. The algae from the phylum *Chlorophyta* can be *Chlorella, Scenedesmus, Dunaliella, Tetraselmis, Haematococcus, Ulva, Codium, Botryococcus* or *Caulerpa* spp. the algae from the phylum *Rhodophyta* can be *Porphyridium cruentum, Gracilaria* sp., *Grateloupia* sp, *Palmaria* sp. *Corallina* sp., *Chondrus crispus, Porphyra* sp. or *Rhodosorus* sp. The algae from the phylum *Heterokontophyta* can be *Nannochlorropsis oculata, Odontella aurita, Phaeodactylum tricornutum. Fucus* sp. *Sargassum* sp. *Padina* sp., *Undaria pinnatifida*, or *Laminaria* sp. The algae from the phylum *Haptophyta* can be *Isochrysis* sp. *Tisochrysis* sp. or Pavlova sp. The algae can be *Chrypthecodinium cohnii, Schizochytrium, Ulkenia* or *Euglena gracilis*. The algae can be a green microalga such as *Chlorella, Scenedesmus, Dunialiella, Haematococcusand Bracteacoccus; haptophyte* microalgae such as *Isochrysis*; and *heterokontophyta* microalgae such as *Phaeodactylum, Ochromonas* and *Odontella.*

In a particular embodiment, the microalga is a green alga. Suitable examples of green alga are *Chlorella* or *Haematyococcus* or *Chlamydomonas*. In another preferred embodiment, the microalga is from genus *Chlamydomonas.*

*Chlamydomonas*, as used herein relates to a genus of green algae consisting of about 325 species all unicellular *flagellates*, found in stagnant water and on damp soil, in freshwater, seawater, and even in snow as "snow algae". In a more preferred embodiment, the microalga is *Chlamydomonas reinhardtii*. In another preferred embodiment, the microalga is *Botryococcus braunii.*

*Chlamydomonas reinhardtii*, as used herein is a single-cell green alga about 10 micrometres in diameter that swims with two flagella. It has a cell wall made of hydroxyprolinerich glycoproteins, a large cup-shaped chloroplast, a large pyrenoid, and an "eyespot" that senses light.

The first and second polynucleotides of interest expressed by the vector of the invention are provided respectively in a first and second expression cassettes, each expression cassette comprising a 5' cis regulatory region and a 3' cis regulatory region operatively linked with the first and second polynucleotides and wherein both the 5' and 3' cis regulatory regions of the first expression cassette are different from the 5' and 3' cis regulatory regions of the second expression cassette.

"Operatively linked" as disclosed herein refers to different DNA fragments joined together such that the amino acid sequences encoded by the DNA fragments remain in-frame. In a still more preferred embodiment, both the 5' and 3' cis regulatory regions of the first expression cassette are different from the 5' and 3' cis regulatory regions of the second expression cassette.

"An expression cassette" as disclosed herein refers to a component of an expression vector comprising one or more polynucleotides of interest and the sequences controlling their expression. Non-limiting basic components of an expression cassette include promoter elements, the gene(s) of interest, and an appropriate mRNA stabilizing polyadenylation signal. Other frequently employed cis-acting elements include internal ribosome entry site (IRES) sequences to allow expression of two or more genes without the need for an additional promoter, introns and post-transcriptional regulatory elements to improve transgene expression. In a preferred embodiment, the vector according to the inventions comprises at least one, at least two or at least three expression cassettes. In a preferred embodiment the vector comprises two expression cassettes.

In a preferred embodiment, the vector of the invention further comprises a third expression cassette comprising a 5' and a 3' cis regulatory regions different from the 5' and 3' cis regulatory regions of the first and second expression cassettes.

In a preferred embodiment, the third expression cassette comprises a selection gene. As it is used herein, the term "selection gene" is a gene, the expression of which creates a detectable phenotype and which facilitates detection of host cells that contain an expression cassette having the selection marker. Non-limiting examples of selection genes include drug resistance genes and nutritional markers. For example, the selection gene can be a gene that confers resistance to an antibiotic selected from the group consisting of: ampicillin, kanamycin, erythromycin, chloramphenicol, gentamycin, kasugamycin, rifampicin, spectinomycin, D-Cycloserine, nalidixic acid, streptomycin, or tetracycline, or to herbicides such as acetoliasa synthase gene (ALS) which confers resistance to the herbicide silfonilurea, or the BAR gene conferring resistence to the herbicide phosphinothricin (PPT). Other non-limiting examples of selection genes include adenosine deaminase, aminoglycoside phosphotransferase, dihydrofolate reductase, hygromycin-B-phosphotransferase, thymidine kinase, and xanthine-guanine phosphoribosyltransferase. A single expression cassette can comprise one or more selection genes such as a nucleotide sequence of shBle gene that codes for bleomycin resistance and can be selected for using bleomycin, a neo gene that codes for kanamycin resistance and can be selected for using kanamycin, G418, etc. Non-limiting-examples of selection genes also include nucleotide sequences encoding a reporter protein. A "reporter protein" as used herein refers to a protein that typically is not present in the recipient organism and typically encodes for proteins resulting in some phenotypic change or enzymatic property which may allow for the selection of transformed cells. Examples of such genes are provided in K. Wising et al. Ann. Rev. Genetics, 22, 421 (1988). Non-limiting examples of reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase (luc) genes from firefly Photinus pyralis. An assay for detecting reporter gene expression may then be performed at a suitable time after said gene has been introduced into recipient cells. One preferred such assay entails the use of the gene encoding beta-glucuronidase (GUS) of the uidA locus of *E. coli* as described by Jefferson et al., (Biochem. Soc. Trans. 15, 17-19 (1987) to identify transformed cells, referred to herein as GUS: 1.

In a preferred embodiment, the expression cassette of the invention comprises as a selection gene a nucleotide sequence of shBle gene (SEQ ID NO: 3) that codes for bleomycin resistance. As disclosed herein, the shBle gene may contain an intron sequence, preferably RBCS2 intron sequence SEQ ID NO 10. More preferably, the shBle contains the RBCS2 intron sequence as disclosed in SEQ ID 22.

The vector of the invention may comprise more than three expression cassettes. Each expression cassette of the vector of the invention comprises a 5' cis regulatory region and a 3' cis regulatory region. A "cis regulatory region" as disclosed herein refers to regions of non-coding DNA which regulate the transcription of neighboring genes. The regulatory region may be located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region. As disclosed herein any known in the art cis regulatory region may be included in the expression cassette. In a preferred embodiment the 5'cis regulatory region comprises: a promoter, a 5'UTR and/or any flanking sequence. In a preferred embodiment the 3'cis regulatory region comprises: 3'UTR, terminator sequences and/or flanking sequences. As used herein, the 5' and/or 3'cis regulatory regions may contain any restriction site at their 5' or 3'end.

As it is used herein, the term "5'-UTR", refers to the sequence at the 5' end of the expression cassette which is not translated and which contains the region necessary for replication, i.e., the sequence which is recognized by the polymerase during synthesis of the RNA molecule from the RNA template. In a preferred embodiment, the 5' untranslated sequence is selected from the group consisting of RPL23, FDX1, HSP70 A, RBCS2, PSAD or any other constitutive highly expressed *Chlamydomonas* gene. Non-limiting examples of 5'UTR include RPL23-5'UTR (SEQ ID NO: 23), FDX-5'UTR (SEQ ID NO: 24) and RBCS2-5'UTR (SEQ ID NO: 25).

As it is used herein, the term "promoter" refers to a nucleic acid sequence which is structurally characterized by the presence of a binding site for the DNA-dependent RNA polymerase, transcription start sites and any other DNA sequence including, but without being limited to, transcription factor binding sites, repressor and activator protein binding sites and any other nucleotide sequence known in the state of the art capable of directly or indirectly regulating transcription from a promoter. Promoter refers to a DNA fragment capable of controlling the expression of a coding sequence or functional RNA. In general, a coding region is located 3' to a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase. In a preferred embodiment, flanking sequences may be operatively linked to the promoter sequences. The term "flanking sequence" refers to a DNA sequence extending on either side of a specific gene sequence. Flanking sequences may be preferably located upstream of the promoter. In the vector of the invention, the 5'cis regulatory region of the expression cassette comprises a sequence selected from the group consisting of the RPL23 promoter, also known as PL (SEQ ID NO: 4), the ferredoxin 1 FDX promoter (SEQ ID NO: 5) and the HSP70-RBCS2chimeric promoter, also known as AR (SEQ ID NO: 6).

In a preferred embodiment the 5'cis regulatory region comprises RPL23 promoter (SEQ ID NO: 4) and RPL23-5'UTR (SEQ ID NO: 23). In a more preferred embodiment the 5'cis regulatory region comprises the RPL23 promoter and RPL23-5'UTR as disclosed in SEQ ID NO 29. In another preferred embodiment, the 5'cis regulatory region is the sequence shown in SEQ ID NO 29.

In a preferred embodiment the 5'cis regulatory region comprises FDX promoter (SEQ ID NO: 5) and FDX 5'UTR (SEQ ID NO: 24). In a more preferred embodiment the 5'cis regulatory region comprises the FDX promoter and FDX-5'UTR as disclosed in SEQ ID NO 31. In another preferred embodiment, the 5'cis regulatory region is the sequence shown in SEQ ID NO: 31.

In a preferred embodiment the 5'cis regulatory region comprises AR chimeric promoter (SEQ ID NO: 6) and 5'UTR RBCS2 (SEQ ID NO: 25). In a more preferred embodiment the 5'UTR comprises additionally the RBCS2 intron sequence (SEQ ID NO 10). In a still more preferred embodiment the 5'cis regulatory region comprises the AR promoter and 5'UTR as disclosed in SEQ ID NO 33. In another preferred embodiment, the 5'cis regulatory region is the sequence shown in SEQ ID NO 33.

As it is used herein, the term "3'-UTR", refers to an untranslated region which appears after the end codon. The 3' untranslated region typically contains a polyadenine tag which allows increasing RNA stability, and therefore the amount of products resulting from the translation of said RNA. As disclosed herein, the 3'UTR sequences may also contain other 3'cis sequences, such as: terminator sequences, flanking sequences and/or any restriction site at their 5' or 3'end. Non-limiting examples of 3'cis sequences include: 3'cis RPL23 (SEQ ID NO 26), 3'cis FDX1 (SEQ ID NO 27) and 3'cis RBCS2 (SEQ ID NO 28). Flanking sequences may be located downstream of 3'UTR. In the vector of the invention the 3' cis regulatory regions comprise a sequence selected from the 3'UTR of the RBCS2 gene, the 3'UTR of the RPL23 gene and 3'UTR of the FDX gene.

In a preferred embodiment the 3'cis regulatory region comprises the 3'UTR RPL23 (SEQ ID NO: 7). In a more preferred embodiment the 3'cis regulatory region comprises additionally the RPL23 terminator and flanking regions (SEQ ID NO: 26). In a still more preferred embodiment the 3'cis regulatory region comprises the 3'UTR RPL23 containing 3'UTR terminator and flanking region as disclosed in SEQ ID NO 30. In another preferred embodiment, the 3'cis regulatory region is the sequence shown in SEQ ID NO: 30.

In a preferred embodiment the 3'cis regulatory region comprises the 3'UTR FDX (SEQ ID NO 9). In a more preferred embodiment the 3'cis regulatory region comprises additionally the FDX terminator and flanking regions (SEQ ID NO: 27). In a still more preferred embodiment the 3'cis regulatory region comprises the 3'UTR FDX containing the 3'UTR terminator and flanking region as disclosed in SEQ ID NO 32. In another preferred embodiment, the 3'cis regulatory region is the sequence shown in SEQ ID NO: 32.

In a preferred embodiment the 3'cis regulatory region comprises the 3'UTR RBCS2 (SEQ ID NO 8). In a more preferred embodiment the 3'cis regulatory region comprises additionally the RBCS2 flanking regions (SEQ ID NO: 28). In a still more preferred embodiment the 3'cis regulatory region comprises the 3'UTR RBCS2 containing the 3'UTR terminator and flanking region as disclosed in SEQ ID NO 34. In another preferred embodiment, the 3'cis regulatory region is the sequence shown in SEQ ID NO: 34.

The poly(A) tag can be of any size provided that it is sufficient to increase stability in the cytoplasm of the molecule of the vector of the invention. In a preferred embodiment, the 3' cis regulatory sequence comprises a sequence selected from the group consisting of 3'UTR of RPL23 (SEQ ID NO: 7), the 3'UTR of the RBCS2 gene (SEQ ID NO: 8) and the 3'UTR of the FDX gene promoter (SEQ ID NO: 9).

In a preferred embodiment, the cis regulatory region comprises a sequence selected from the group consisting of a HSP70A/RBCS2 chimeric promoter (SEQ ID NO: 6), the RPL23 gene promoter (SEQ ID NO: 4), the FDX gene promoter (SEQ ID NO: 5), the 3'UTR of the RBCS2 gene (SEQ ID NO: 8), the 3'UTR of the RPL23 gene (SEQ ID NO: 7), 3'UTR of the FDX gene (SEQ ID NO: 9) and any combination thereof.

In a more preferred embodiment, the 5' cis regulatory region comprises a sequence selected from the group consisting of the HSP70A/RBCS2 chimeric promoter (SEQ ID NO: 6), the RPL23 gene promoter (SEQ ID NO: 4) and the FDX gene promoter (SEQ ID NO: 5), and the 3' cis regulatory region comprises a sequence selected from the group consisting of 3'UTR of the RBCS2 gene (SEQ ID NO: 8), the 3'UTR of the RPL23 gene (SEQ ID NO: 7) and the 3'UTR of the FDX gene (SEQ ID NO: 9).

In a preferred embodiment, the cis regulatory regions in one of the expression cassettes comprises a sequence selected from the group consisting of HSP70A/RBCS2 chimeric promoter (SEQ ID NO: 6) and 3'UTR of the RBCS2 gene (SEQ ID NO: 8), HSP70A/RBCS2 chimeric promoter (SEQ ID NO: 6) and the 3'UTR of the RPL23 gene (SEQ ID NO: 7); and HSP70A/RBCS2 chimeric promoter (SEQ ID NO: 6) and 3'UTR of the FDX gene (SEQ ID NO: 9).

In another preferred embodiment, the cis regulatory regions in one expression cassette comprises a sequence selected from the group consisting of RPL23 gene promoter (SEQ ID NO: 4) and 3'UTR of the RBCS2 gene (SEQ ID NO: 8), RPL23 gene promoter (SEQ ID NO: 4) and the 3'UTR of the RPL23 gene (SEQ ID NO: 7); and RPL23 gene promoter (SEQ ID NO: 4) and 3'UTR of the FDX gene (SEQ ID NO: 9).

In another preferred embodiment, the cis regulatory regions in one expression cassette comprises a sequence selected from the group consisting of FDX gene promoter (SEQ ID NO: 5), and 3'UTR of the RBCS2 gene (SEQ ID NO: 8), FDX gene promoter (SEQ ID NO: 5) and the 3'UTR of the RPL23 gene (SEQ ID NO: 7); and FDX gene promoter (SEQ ID NO: 5), and 3'UTR of the FDX gene (SEQ ID NO: 9).

In another preferred embodiment, the 5'cis regulatory regions in one expression cassette is selected from the sequences shown in SEQ ID NO 29, SEQ ID NO: 31 and SEQ ID NO: 33. In another preferred embodiment, the 3'cis regulatory regions in one expression cassette is selected from the sequences shown in SEQ ID NO 30, SEQ ID NO: 32 and SEQ ID NO: 34.

In a still more preferred embodiment the sequence comprising HSP70A/RBCS2 chimeric promoter and the sequence comprising the 3'UTR of the RBCS2 are in one of the cassettes, the sequence comprising RPL23 gene promoter and the sequence comprising 3'UTR of the RPL23 gene are in a different cassette, and the sequence comprising FDX gene promoter and sequence comprising the 3'UTR of the FDX gene are in a cassette different from the other two.

In a preferred embodiment, the third expression cassette comprises the HSP70A/RBCS2 chimeric promoter and the 3'UTR of the RBCS2 gene as cis regulatory regions.

In a preferred embodiment, the 5' and 3' cis regulatory regions in the first expression cassette are respectively a sequence comprising the RPL23 gene promoter (SEQ ID NO: 4) and the 3'UTR of the RPL23 gene (SEQ ID NO: 7) and the 5' and 3' regulatory regions of the second expression cassette are respectively a sequence comprising the FDX gene promoter (SEQ ID NO: 5) and the 3'UTR of the FDX gene (SEQ ID NO: 9).

In another preferred embodiment of the vector of the invention, the polynucleotide of interest within at least one of the expression cassettes encodes a protein of interest and said expression cassette comprises an intron sequence within the region encoding the protein of interest or the protein encoded by the selection gene and/or a nucleotide sequence encoding a signal peptide in the same open reading frame at position 5' respect to the nucleotide sequence encoding the protein of interest or the protein encoded by the selection gene.

In a preferred embodiment, the vector comprises a first expression cassette comprising a polynucleotide encoding the light chain of an antibody, the RPL23 gene promoter and the 3'UTR of the RPL23 gene, the second expression cassette comprises the FDX gene promoter, the 3'UTR of the FDX gene and a polynucleotide encoding the heavy chain of the antibody, and the third expression cassette comprises the bleomycin resistance gene, the HSP70A/RBCS2 chimeric promoter and the 3'UTR of the RBCS2 gene as cis regulatory regions.

As it is used herein, the term "intron" or "intron sequence" refers to any nucleotide sequence within a gene that is removed by RNA splicing during maturation of the final RNA product. The term intron refers to both the DNA sequence within a gene and the corresponding sequence in RNA transcripts. In a preferred embodiment, the polynucleotide of interest within at least one of the expression cassettes comprises an intron within any of the expression cassette components. In a more preferred embodiment, at least one of the expression cassettes comprises an intron within the polynucleotide of interest, the region encoding the protein of interest or the selection gene. In a still more preferred embodiment the intron is a RBCS2 intron having the sequence shown in SEQ ID NO: 10.

In another preferred embodiment, at least one of the expression cassettes comprises a nucleotide sequence encoding a signal peptide in the same open reading frame at position 5' respect to the nucleotide sequence encoding the protein of interest or the protein encoded by the selection gene.

As it is used herein, the term "signal peptide" or "secretory signal peptide" refers to a peptide of a relatively short length, generally between 5 and 30 amino acid residues, directing proteins synthesized in the cell towards the secretory pathway. The signal peptide usually contains a series of hydrophobic amino acids adopting a secondary alpha helix structure. Additionally, many peptides include a series of positively-charged amino acids that can contribute to the protein adopting the suitable topology for its translocation. The signal peptide tends to have at its carboxyl end a motif for recognition by a peptidase, which is capable of hydrolyzing the signal peptide giving rise to a free signal peptide and a mature protein. The signal peptide can be cleaved once the protein of interest has reached the appropriate location. Any secretory signal peptide may be used in the present invention. As a way of illustrative non limitative examples signal peptide from *Chlamydomonas reinhardtii* carbonic anhydrase (CAH1) (SEQ ID NO: 12), signal peptide from *Chlamydomonas reinhardtii* periplasmic arylsulfatase (ARS1) (SEQ ID NO: 14) or the signal peptide from *Chlamydomonas reinhardtii* Gametolysin M11 (SEQ ID NO: 16) may be used. In a preferred embodiment CAH1 signal peptide is encoded by SEQ ID NO: 11, ARS1 signal peptide is encoded by SEQ ID NO: 13 and Gametolysin M11 signal peptide is encoded by SEQ ID NO: 15.

In a preferred embodiment the sequence encoding the signal peptide is in the same open reading frame at position 5' respect to the nucleotide sequence encoding the polynucleotide of interest. In a more preferred embodiment, the polynucleotide of interest encodes a protein of interest. In another preferred embodiment the sequence encoding the signal peptide is in the same open reading frame at position 5' respect to the selection gene. In a preferred embodiment the signal peptide is a murine signal peptide. In a more preferred embodiment, the murine signal peptide is selected from SEQ ID NO 20 and SEQ ID NO 21. In a still more preferred embodiment, the sequence encoding the murine signal peptide is selected from SEQ ID 17 and SEQ ID 18. Fusion of signal peptide to the protein of interest results in secretion of the fusion protein to media, which is the preferred strategy since it permits easy and efficient purification from the extracellular medium. In addition, the secretory production of recombinant proteins has the advantage that proteolytic degradation may be avoided and that there is a better chance of correct protein folding.

Host Cell

In another aspect the invention relates to a host cell comprising a vector as described previously.

The term "host cell" is used such that it refers not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic (e.g., *E. coli*) or eukaryotic cell (e.g., yeast or plant cells).

In a preferred embodiment the host cell is a microalga. In a more preferred embodiment, the host cell is a green microalga. In a more preferred embodiment the host cell is from genus *Chlamydomonas*.

In a more preferred embodiment the host cell is *C. reinhardtii.*

The invention also relates to the use of the vector according to the invention or a host cell according to the invention for simultaneously co-expressing the first and second polynucleotide of interest.

In a preferred embodiment, the co-expression of the first and second polynucleotide of interest is stoichiometric.

In another preferred embodiment the first polynucleotide of interest encodes a protein of interest. In another preferred embodiment the first and second polynucleotide of interest encode a protein of interest. In a more preferred embodiment the first and second protein of interest are co-expressed. In a still more preferred embodiment the co-expression of the first and second protein of interest is stoichiometric. As disclosed herein "stoichiometric manner" or "stoichiometric" means that the two polynucleotides and/or proteins of interest are expressed at the same level (1:1).

All the terms and embodiments previously described are equally applicable to this aspect of the invention.

a Method for Co-Expressing Two Polynucleotides of Interest

In another aspect the invention relates to a method for co-expressing two polynucleotides of interest which comprises growing a cell carrying a vector according to the invention in conditions suitable for allowing the expression of the polynucleotides of interest.

The method of the invention may comprise a first step of introducing in a microalga cell a vector according to the invention. The vector of the invention may be introduced into a microalga by means of well-known *Chlamydomonas* nuclear transformation techniques such as transfection (that may be chemical or non-chemical such as glass beads), electroporation and particle bombardment using the vector of the invention that has been isolated. In a preferred embodiment the vector is introduced by transformation. The transformed algae may be recovered on a solid nutrient media or in liquid media.

In addition, the method of the invention may comprise growing said cell in conditions suitable for allowing the co-expression of the polynucleotides interest. Culture conditions suitable for the growth of the microalga and for the expression of the protein of interest may be different for each type of microalga. However, those conditions are known by skilled workers and are readily determined. In a particular embodiment, the microalga is grown under mixotrophic conditions. In a particular embodiment, the microalga is cultured in a photobioreactor in a suitable medium, under a suitable luminous intensity, at a suitable temperature. Practically any medium suitable for growing microalgae can be used; nevertheless, illustrative, non-limitative examples of said media include TAP media. The luminous intensity can vary widely, nevertheless, in a particular embodiment, the luminous intensity is comprised between 25 and 150 μmol photons m-2 s-1, particularly 100 uE. The temperature can vary usually between about 17° C. and about 30° C., particularly 25° C. The culture can be performed in the absence of aeration or with aeration. Similarly, the duration of maintenance can differ with the microalga and with the amount of protein desired to be prepared. Again, those conditions are well known and can readily be determined in specific situations. In a preferred embodiment the microalga is a green alga, more particularly from genus *Chlamydomonas*, and more particularly *Chlamydomonas reinhardtii.*

In a preferred embodiment the first polynucleotide of interest encodes a protein of interest. In another preferred embodiment the first and second polynucleotide of interest encode a protein of interest.

In a particular embodiment, the method of the invention further comprises purifying the protein of interest. Suitable purification can be carried out by methods known to the person skilled in the art such as by using lysis methods, extraction, ion exchange resins, electrodialysis, nanofiltration, etc.

In a preferred embodiment, the co-expression of the first and second proteins of interest is stoichiometric. Thus, if stoichiometric levels of the two proteins are not detected, an additional vector may be introduced into the cell having a vector of the invention. The detection of the two proteins of interest can be done within a purified sample, cell culture media or whole cell extracts (total culture).

Thus, in a particular embodiment, the method of the invention further comprises growing a cell carrying a second expression vector comprising the first or second expression cassette used in the first expression vector according to the invention. In a preferred embodiment when the expression and/or secretion of one of the proteins of interest is not stoichiometric (1:1) in relation to the expression and/or secretion of the other protein of interest, the selected cell is retransformed with a second expression vector comprising an expression cassette encoding the protein of interest with the lowest expression and/or secretion. As used herein, the non-stoichiometric expression may lead to an insoluble, inactive or unstable heterodimer.

In a preferred embodiment the second expression vector comprises an expression cassette comprising a nucleotide sequence of a selection gene different from the selection gene used in the vector used for the expression of the first and second proteins of interest. In a preferred embodiment the selection gene found in the second vector is the paromomycin (paro) resistance gene (SEQ ID 19). In a preferred embodiment the second transformants with an expression vector according to the invention are selected on paromomycin (paro) containing plates.

All the terms and embodiments previously described are equally applicable to this aspect of the invention.

a Method for Selecting a Cell

In another aspect the invention relates to a method for selecting a cell co-expressing in a stoichiometric manner two proteins of interest, comprising a) transforming a cell with a vector according to the invention,
b) detecting the expression of the two proteins of interest, and
c) selecting a cell expressing the two proteins of interest in a stoichiometric manner.

In a preferred embodiment the method for detecting the expression of the two proteins of interest is performed upon total culture, which includes media and cells that were previously disrupted by a cycle of freeze/thaw. In a preferred embodiment the expression of the two proteins of interest is detected by sandwich ELISA.

In a preferred embodiment the two proteins of interest are the heavy chain and the light chain of an antibody. In a more preferred embodiment the two proteins of interest are detected by an antibody specific for Fc region and an antibody specific for F(ab) 2 region.

All the terms and embodiments previously described are equally applicable to this aspect of the invention.

The invention will be described by way of the following examples which are to be considered as merely illustrative and not limitative of the scope of the invention.

EXAMPLES

Example 1—Vector Construction

Expression strategy is based on the design of a single vector (FIG. 1) containing three cassettes: one for the expression of an antibiotic resistance for initial selection of transformants ($Ble^R$), one for the expression of the heavy chain (HC) and one for the expression of the light chain (LC). Because use of multiple copies of transgene arranged in tandem are associated with low transgene expression (Garrick et al. 1998 Nat Genet. 18 (1): 56-9) use of repetitive elements in one single vector, such as same cis regulatory elements to drive multiple gene expression, may also cause a decreased transgene expression. To increase probability of multiple high transgene expression three different cis regulatory regions (5' and 3') were included in a single vector to drive expression of a monoclonal antibody as an example of dimeric protein: HSP70A/RBCS2 (AR) promoter and 5'UTR RBCS2 (containing RBCS2 intron as previously described and 3'UTR RBCS2 to drive expression of bleomycin resistance, Ferredoxin 1 (FDX1, also called PETF) (Cre14.g626700) cis regulatory regions (5' and 3') to drive expression of the heavy chain (HC) and *Chlamydomonas* Ribosomal protein L23 (RPL23) (Cre04.g211800) cis regulatory regions to drive light chain (LC) expression. The FDX1 and RPL23 cis regulatory regions have been recently described (López-Paz et al. 2017). AR quimeric promoter, including also an intron of RBCS2 has been also previously used (Heitzer and Zschoernig 2007 BioTechniques 43:324-328. HC and LC sequences were codon adapted with IDT web tool (eu.idtdna.com/CodonOpt) and murine signal sequence was taken from the original murine antibody sequence.

Examples 2—Screening of mAb Production in *Chlamydomonas* Transformants

The high variability in expression levels among *Chlamydomonas* transformants makes necessary the development of a high throughput screening to select the highest expressing transformants, therefore, a rapid sandwich ELISA was developed to identify clones expressing both heavy and light chain. Briefly, initial transformants were selected on zeocin containing plates, individually picked and grown in 96 well plates until reaching stationary phase. Since we had no information if the used murine signal peptide would be functional in *Chlamydomonas* our screening was performed with total culture (this includes media and cells that were previously disrupted by a cycle of freeze/thaw). Presence of fully assembled antibody was determined by a sandwich ELISA where capture antibody was an Anti-Mouse IgG, Fc-y Fragment Specific antibody, and detection antibody was a conjugated anti-mouse IgG, F(ab') 2 fragment specific. As a positive control and as a reference of assay sensitivity serial dilutions of purified 5mC3 (CHO produced) were used to create a standard trend line. The inclusion in the assay of standard curves containing wild type cell extract or culture media showed that neither the crude cell extract nor culture media prevented the mAb from being recognized by the used antibodies. Values obtained with non transformed strains (media or total culture extracts) served as references of background signal.

Figure 2:
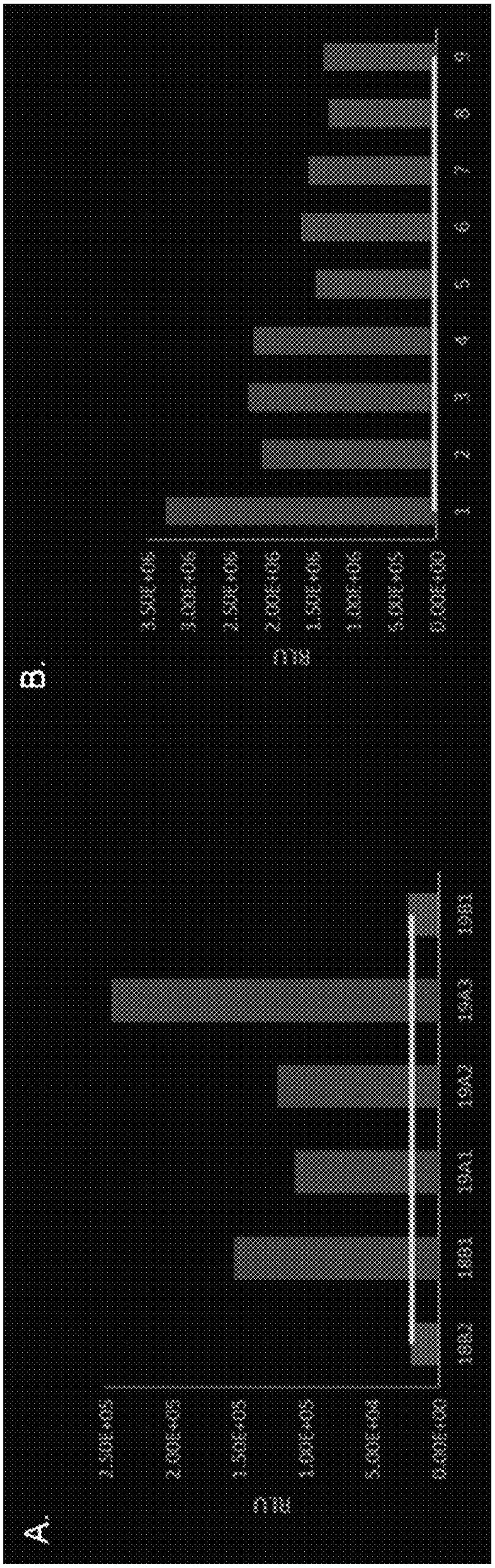
FIGS. 2A-B. Sandwich ELISA results of positive selected *Chlamydomonas* clones expressing m5C3 monoclonal antibody. Results of initially identified in FIG. 2A CC-124 and in FIG. 2B UVM4 positive transformants are expressed as RLU (Relative Luminiscence Units). Mean background levels is represented as a thick line.

Two different strains were used to test the expression of recombinant m5C3 antibody: wild type CC-124 and mutant strain UVM4. For the case of CC-124 strain, four out of 184 transformants showed, at least, 5-fold signal increase relative to background (represented by a line in FIG. 2) and were selected for further analysis (18B1, 19A1, 19A2 and 19A3). Results of two transformants considered not positive are also shown (FIG. 2: 18B2 and 19B1). For the case of UVM4 (Neupert et al, 2009. The Plant Journal. 57:1140-1150), a mutant reported to express transgenes to higher levels), 9 out of 96 initial transformants (resistant to 15 μg/ml zeocin) showed, at least, a 50-fold signal increase relative to background (represented by a line in FIG. 2). Four transformants were selected with the highest expression that showed, at least, a 100-fold signal increase relative to mean value.

Figure 3A:
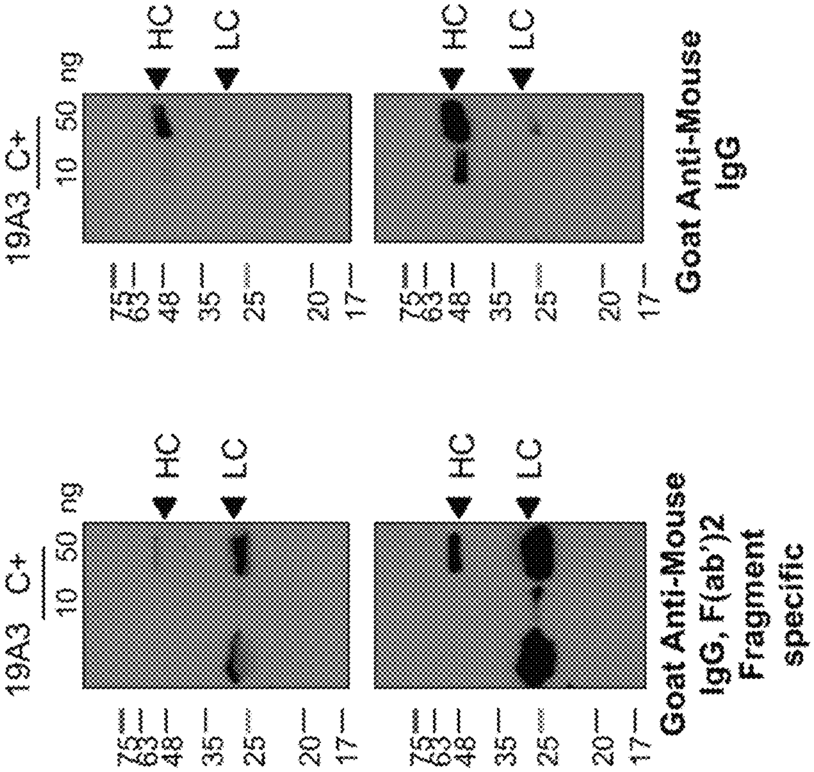
FIGS. 3A-3C. Immunoblot evaluation of mAb expressed by CC-124 and UVM4 selected transformants.
Figure 3B:
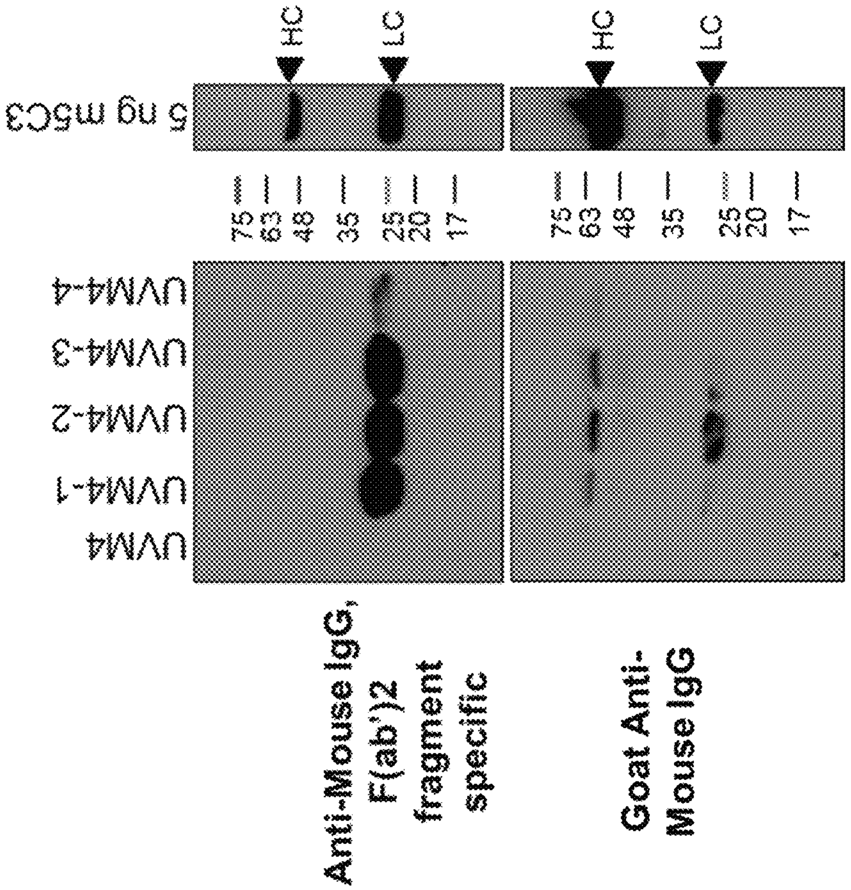
Figure 3C:
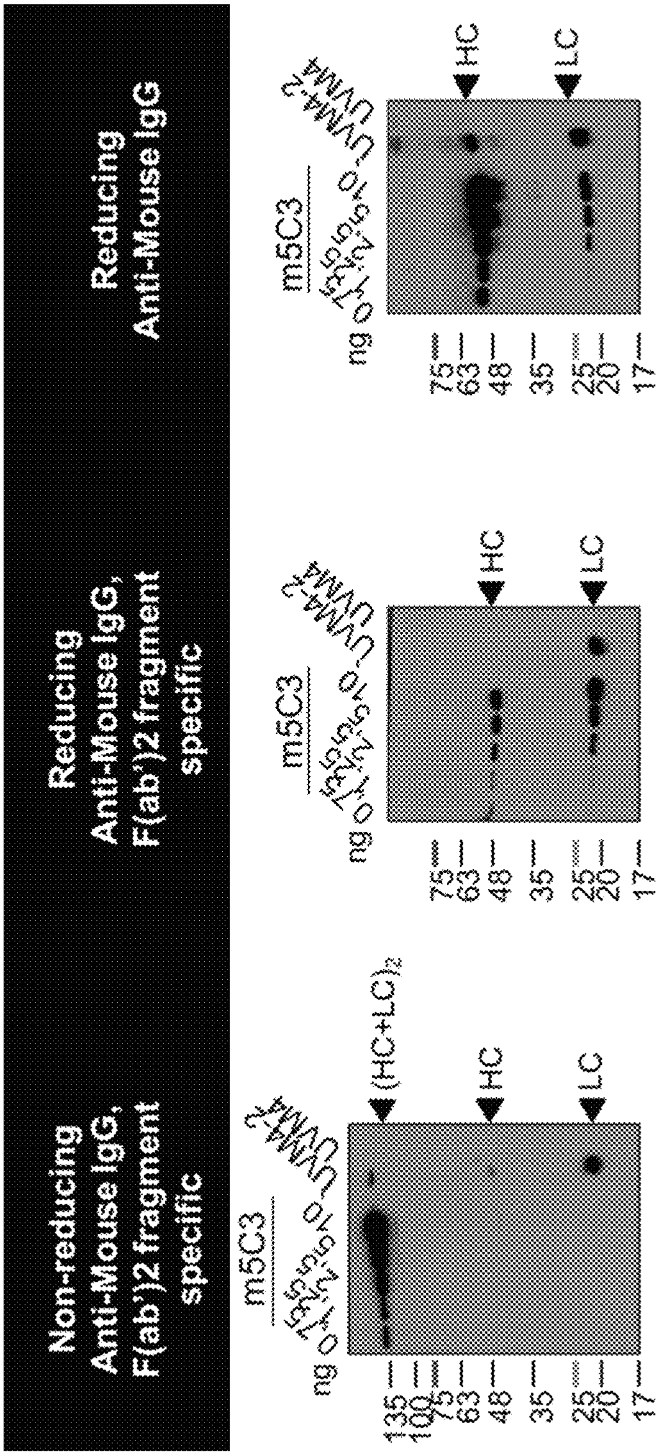

Expression of both chains was analyzed by western blot since the used anti-mouse IgG that reacts with F(ab') 2 region may also react with single heavy chain—although with less affinity than for the light chain or Fab2 domain-and therefore it is possible to obtain signal in clones that express only heavy chain. The immunoblot was performed using an anti-mouse IgG that preferentially detects the heavy chain, and an anti-mouse F(ab') 2 region (FIG. 3). Clone 19A3 was selected for western blot analysis since it showed maximum signal by Sandwich ELISA. Surprisingly, whereas, light chain was detected by immunoblot in concentrated clarified media, no heavy chain was detected in clone 19A3. In the case of UVM4 positive transformants, it was possible to detect both light and heavy chain, although expression of light chain was in all cases significantly higher than expression of heavy chain. This result may not be due to lower transcription/translational effectiveness of FDX1 promoter/regulatory regions compared to RPL23 regions but may account for the lower unstability or secretion of heavy chain vs light chain. (FIG. 3). Importantly, no band or signal was detected in UVM4 or CC124 negative controls with any of the antibodies used. Under reducing conditions both antibody chains are detected separately, whereas in non-reduced SDS-PAGE a high molecular weight signal is detected, which corresponds to the fully-assembled antibody (FIG. 3C). Under both conditions (denaturing and non-denaturing) it can be observed that stoichiometry differs from 5C3 antibody expressed in mammalian cells: LC is overexpressed relative to HC, presumably due to poor expression/secretion or instability of this chain.

In order to increase expression of the heavy chain antibody, and consequently, levels of fully assembled antibody, clone 19A3 was retransformed with a vector containing only heavy chain plus a different selectable marker. A similar ELISA sandwich screening was performed with this second round of transformants and clones with signal above the mean value (signal in the range of 19A3 signal) were selected for further characterization.

Example 3—Retransformation and Screening of Transformants

Figure 4:
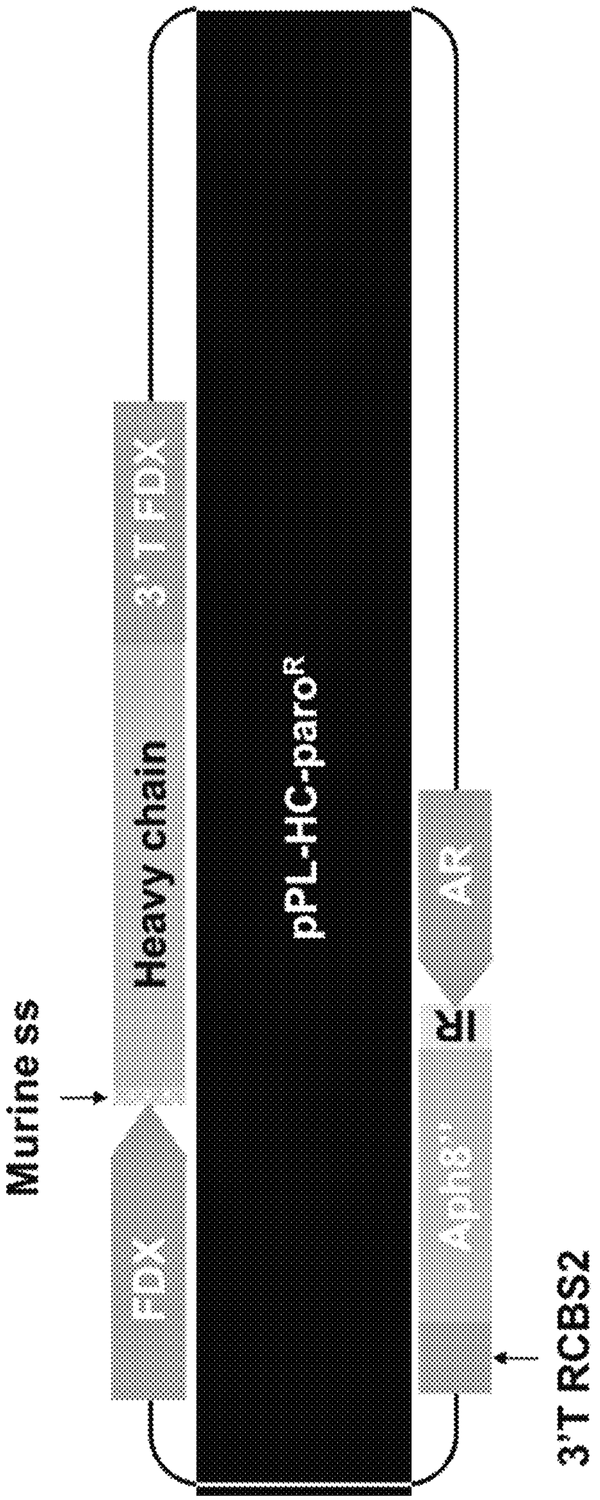
FIG. 4. HC-paro$^R$ vector map. AR: HSP70-RBCS2 chimeric promoter (including 5'UTR and intron of RBCS2), IR: intron 1 of RBCS2. FDX: ferredoxin 1 cis regulatory elements. Aph8: paromomycin resistant gene.
Figure 5A:
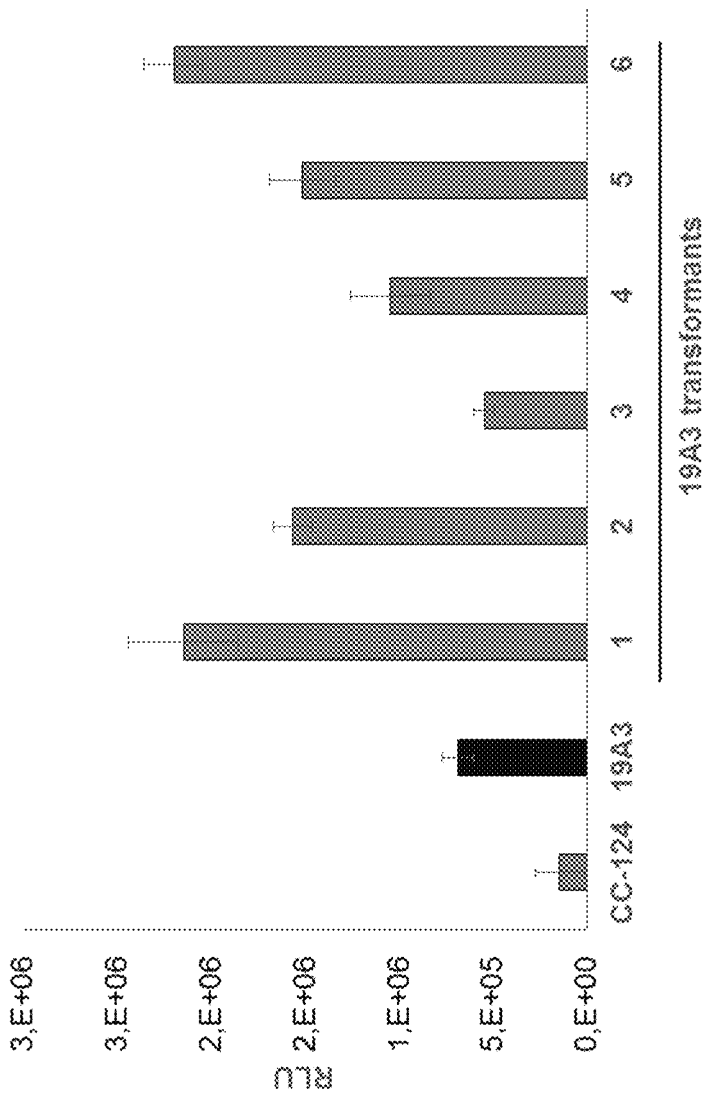
FIGS. 5A-B. Analysis of antibody expression and assembly of positive identified retransformants.
Figure 5B:
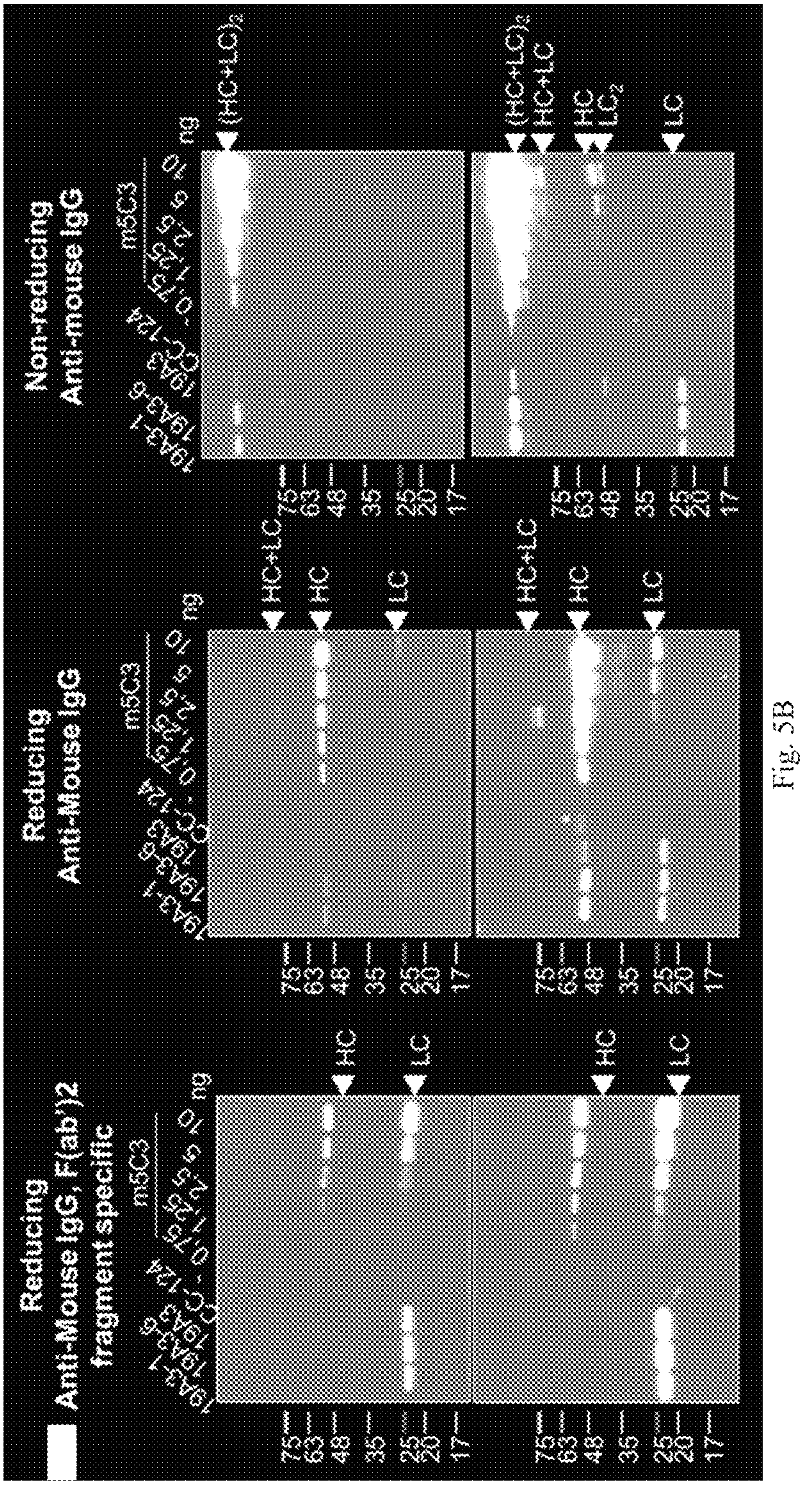
Figure 6:
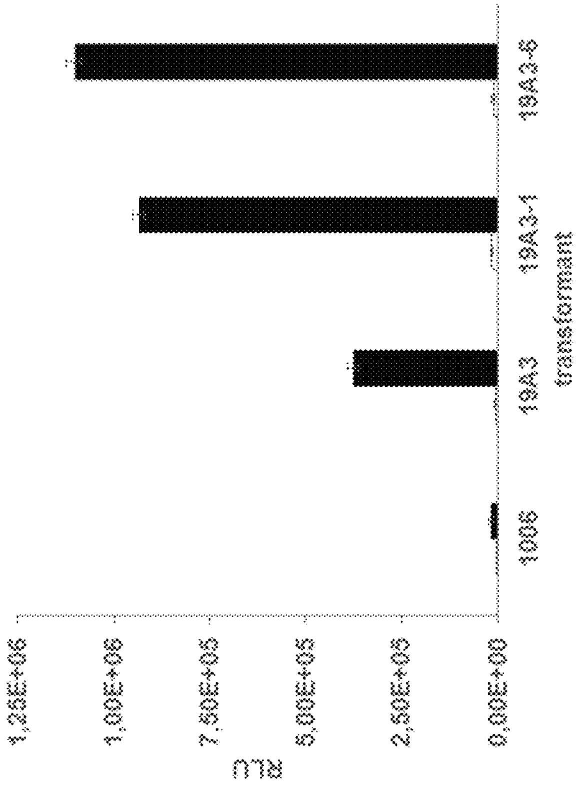
FIGS. 6A-B. Quantification of secreted and intracellular mAb concentration in selected clones.
Figure 7A:
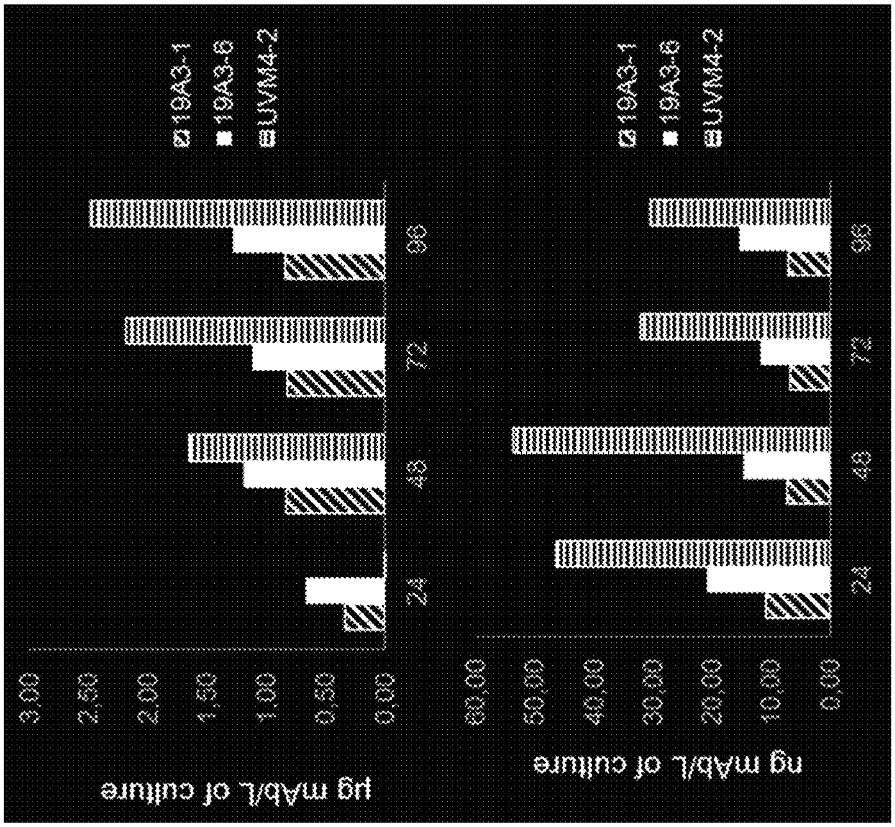
FIGS. 7A-7D. Time course of mAb expression and assembly during exponential and stationary phases.
Figure 7B:
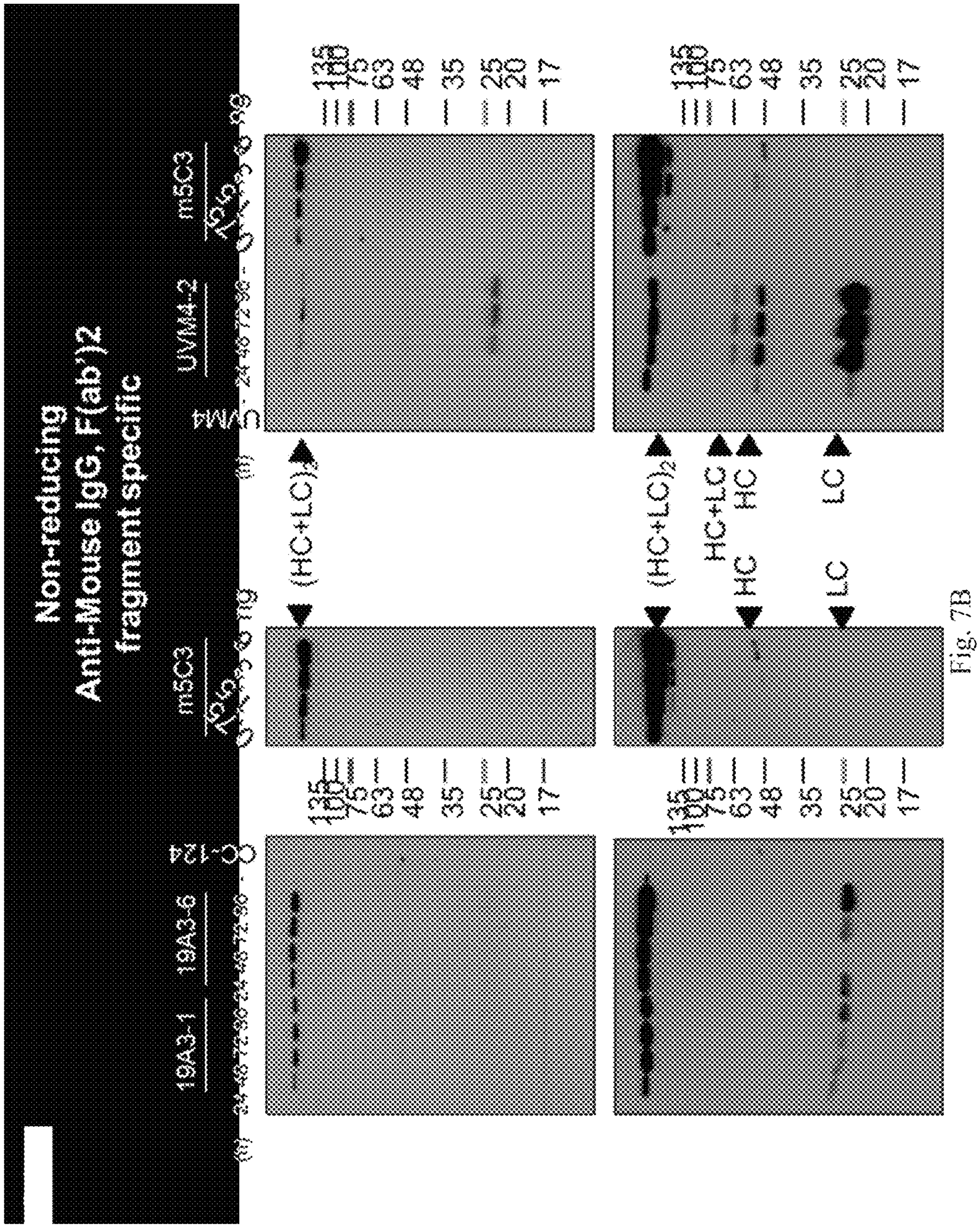
Figure 7C:
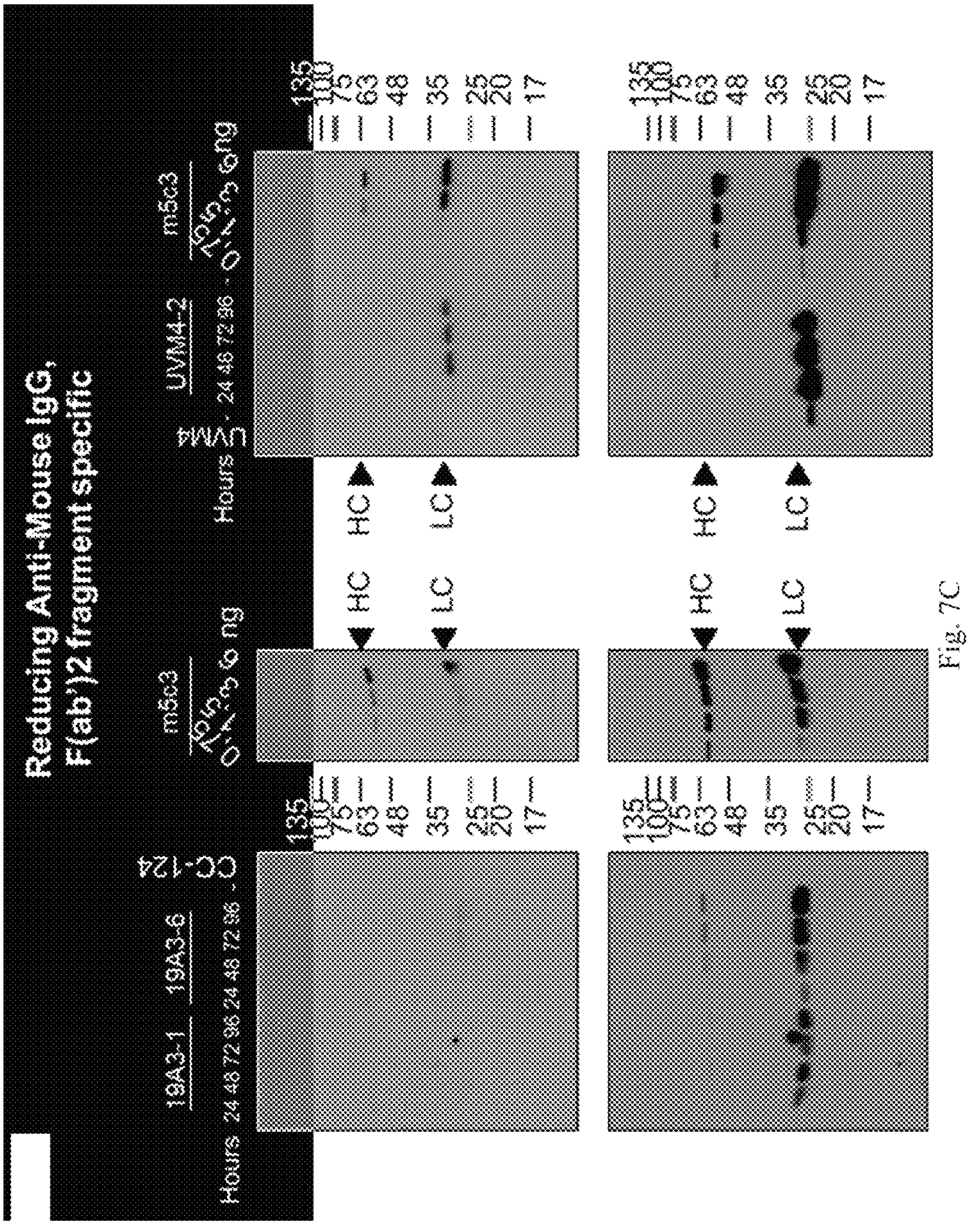
Figure 7D:
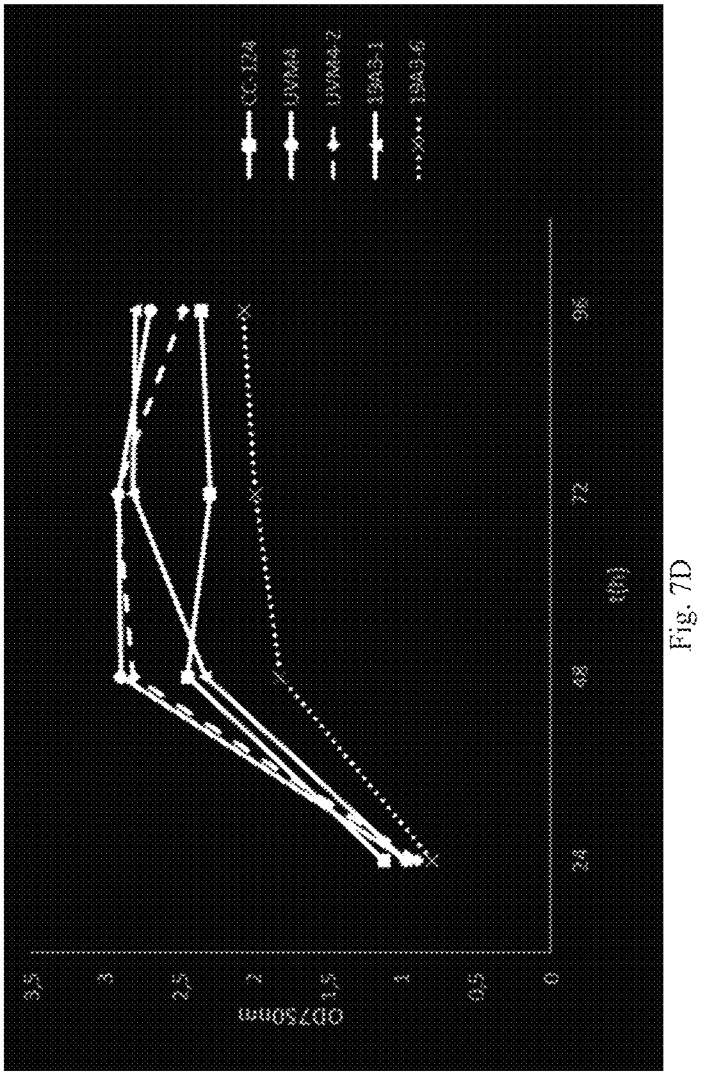

HC-paro$^{R}$ vector (FIG. 4) was transformed into 19A3 clone and 376 initial transformants (resistant to 25 μg/ml paromomycin) were analyzed by sandwich ELISA as reported previously. In this second ELISA, the median RLU value of all the initial transformants (that was similar to 19A3 signal) was taken as background. Clones that showed a 3-fold RLU signal above background were considered positives and were selected for further analysis (19A3 #1 and 19A3 #6) (FIG. 5). Quantification by Sandwich ELISA of mAb expression in both cells and clarified media revealed that in both transformants accumulation occurred mainly in the media (only 1% of total mAb was found in cell extracts) and therefore, clarified media was used in the following analysis. The standard curve included in the assay (m5c3 purified mAb) allowed the estimation of the mAb expressed (FIG. 6).

To evaluate expression of fully assembled mAb in the selected transformants (19A3 #1, 19A #6 and 19A3) an immunoblot analysis was performed. Immunoblots were performed using an anti-mouse IgG and an anti-mouse IgG specific for F(ab') 2 region under reducing and non-reducing conditions (FIG. 5B). Results showed that increase on RLU expression correlated with increased heavy chain expression in retransformed clones and, accordingly, with an increase in the expression of fully assembled mAb. ELISA sandwich and Inmmunoblot assays validate our high-throughput screening method and demonstrates that *Chlamydomonas* may express and secrete fully assemble mammalian monoclonal antibodies.

Expression of mAb in selected clones was estimated on the base of these immunoblots. Based on the non-reducing immunoblot approximately 0.4 μg/L of complete mAb was estimated in clones 19A #1 and 19A #6 and approximately 0.1 μg/L was estimated in 19A3 transformant. Based on the reducing immunoblot using anti-Fab, approximately 1.5 μg/L of light chain were estimated in 19A #1, 19A3 #6 and 19A3 transformants. In the case of heavy chain, based on the reducing immunoblot with anti-Fc region around a 0.2 μg/L were estimated for clones #1 and #6 whereas the heavy chain was too low to be quantifiable in 19A3 transformant. That estimation of expression corroborates that the increase on heavy chain copy number resulted in an increase on the expression of complete mAb. Note that since insertion of transgene during transformation occurs randomly in the genome, probability of second copy being inserted next to first insertion is low and so it is the probability of silencing due to multiple copy arrangement.

Examples 4—mAb Characterization in Selected Transformants mAb expression in selected tranformants (19A3 #1, 19A3 #6 and UVM4 #2) was monitored at different stages of growth. Quantification in samples (extracellular and intracellular) was done by sandwich ELISA, using a standard curve of purified mouse m5C3. Growth rate was monitored by $OD_{750nm}$ and no significant differences were observed between transformed and wild type strains (FIG. 7).

The invention claimed is:

1. An expression vector for the co-expression of a first and second polynucleotides of interest in microalgal cells, wherein said first and second polynucleotides of interest are provided respectively in a first and second expression cassettes, each expression cassette comprising a 5' cis regulatory region and a 3' cis regulatory region operatively linked with the first and second polynucleotides,
   - wherein the 5' and 3' cis regulatory regions in the first expression cassette comprise, respectively, an RPL23 gene promoter and a 3'UTR of the RPL23 gene, and the 5' and 3' cis regulatory regions of the second expression cassette comprise respectively an FDX gene promoter and a 3'UTR of the FDX gene,
   - wherein the expression vector further comprises a third expression cassette comprising a HSP70A/RBCS2 chimeric promoter and a 3'UTR of the RBCS2 gene as cis regulatory regions, and
   - wherein the first and second polynucleotide encode two different subunits of a heterodimeric protein.

2. The vector according to claim 1, wherein the third expression cassette comprises a selection gene.

3. The vector according to claim 2, wherein the selection gene is bleomycin resistance gene.

4. The vector according to claim 2, further comprising
   - (a) an intron sequence within a region encoding the first or second subunit of the heterodimeric protein or within a region encoding the selection gene, and/or
   - (b) a nucleotide sequence encoding a signal peptide 5' of and operably linked to the nucleotide sequence encoding (i) the first subunit of the heterodimeric protein, (ii) the second subunit of the heterodimeric protein, and/or (iii) the protein encoded by the selection gene.

5. The vector according to claim 4, wherein the signal peptide is a murine signal peptide.

6. The vector according to claim 1, wherein the first and second polynucleotides are codon optimized for expression in microalgal cells.

7. The vector according to claim 1, wherein the first and second subunits are the heavy chain or a fragment thereof and the light chain or a fragment thereof of an antibody.

8. The vector according to claim 1, wherein the first expression cassette comprises a polynucleotide encoding the light chain of an antibody, the second expression cassette comprises polynucleotide encoding the heavy chain of the antibody and the third expression cassette comprises the bleomycin resistance gene.

9. A host cell comprising a vector according to claim 1, wherein the host cell is a microalga.

10. The host cell according to claim 9, wherein the microalga is from genus *Chlamydomonas*.

11. The host cell according to claim 10, wherein the microalga is *C. reinhardtii*.

12. A method for co-expressing a first and second polynucleotides of interest encoding a first and second subunit of a heterodimeric protein comprising growing a cell carrying the vector according to claim 1, in conditions suitable for allowing the expression of the polynucleotides of interest.

13. A method for selecting a cell co-expressing in a stoichiometric manner two subunits of a heterodimeric protein, comprising a) transforming a cell with the vector according to claim 1, b) detecting the expression of the two subunits, and c) selecting a cell expressing the two subunits in a stoichiometric manner.

14. The method according to claim 13, wherein the two subunits of the heterodimeric protein are a heavy chain or a fragment thereof and a light chain or a fragment thereof of an antibody, and wherein step b) is performed by an antibody selected from an antibody specific for the Fc, region, an antibody specific for the F(ab') 2 region and a combination thereof.

* * * * *